(12) United States Patent
Elbasiony et al.

(10) Patent No.: US 9,173,591 B2
(45) Date of Patent: Nov. 3, 2015

(54) STENT VISUALIZATION AND MALAPPOSITION DETECTION SYSTEMS, DEVICES, AND METHODS

(71) Applicants: Amr Elbasiony, Chelmsford, MA (US); Joel Friedman, Andover, MA (US)

(72) Inventors: Amr Elbasiony, Chelmsford, MA (US); Joel Friedman, Andover, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 54 days.

(21) Appl. No.: 13/790,587

(22) Filed: Mar. 8, 2013

(65) Prior Publication Data
US 2014/0257087 A1    Sep. 11, 2014

(51) Int. Cl.
*A61B 5/06* (2006.01)
*A61B 5/00* (2006.01)

(52) U.S. Cl.
CPC .............. *A61B 5/061* (2013.01); *A61B 5/0066* (2013.01); *A61B 2505/05* (2013.01)

(58) Field of Classification Search
CPC ... A61B 5/061; A61B 5/0066; A61B 2505/05
USPC ........................... 600/407–480; 382/128–132
See application file for complete search history.

(56) References Cited

U.S. PATENT DOCUMENTS

| | | |
|---|---|---|
| 5,054,492 A | 10/1991 | Scribner et al. |
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,531,227 A | 7/1996 | Schneider |
| 5,619,368 A | 4/1997 | Swanson |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,956,355 A | 9/1999 | Swanson et al. |
| 5,989,189 A | 11/1999 | LeBlanc et al. |

(Continued)

FOREIGN PATENT DOCUMENTS

| | | |
|---|---|---|
| WO | 2006076409 | 7/2006 |
| WO | 2007002685 | 1/2007 |
| WO | 2011038044 | 3/2011 |

OTHER PUBLICATIONS

Bonnema et al., "An automatic algorithm for detecting stent endothelialization from volumetric optical coherence tomography datasets", Physics in Medicine and Biology, 53:12, Jun. 21, 2008, pp. 3083-3098.

(Continued)

*Primary Examiner* — Sanjay Cattungal
(74) *Attorney, Agent, or Firm* — K&L Gates LLP

(57) ABSTRACT

In part, the invention relates to computer-based methods, devices, and systems suitable for displaying stent malapposition in a 2-D or 3-D image. A threshold malapposition distance can be set as an input in response to which a software component in an imaging pipeline automatically detects stent struts and calculates a malapposition distance from a lumen contour. Projections of stent strut dimensions can be used to compensate for stent imaging artifacts results from imaging probe orientation in the lumen.

19 Claims, 14 Drawing Sheets

(56) References Cited

U.S. PATENT DOCUMENTS

| | | | |
|---|---|---|---|
| 6,111,645 | A | 8/2000 | Tearney et al. |
| 6,134,003 | A | 10/2000 | Tearney et al. |
| 6,148,095 | A | 11/2000 | Prause et al. |
| 6,160,826 | A | 12/2000 | Swanson et al. |
| 6,191,862 | B1 | 2/2001 | Swanson et al. |
| 6,208,883 | B1 | 3/2001 | Holupka et al. |
| 6,282,011 | B1 | 8/2001 | Tearney et al. |
| 6,421,164 | B2 | 7/2002 | Tearney et al. |
| 6,445,939 | B1 | 9/2002 | Swanson et al. |
| 6,485,413 | B1 | 11/2002 | Boppart et al. |
| 6,501,551 | B1 | 12/2002 | Tearney et al. |
| 6,552,796 | B2 | 4/2003 | Magnin et al. |
| 6,564,087 | B1 | 5/2003 | Pitris et al. |
| 6,570,659 | B2 | 5/2003 | Schmitt |
| 6,706,004 | B2 | 3/2004 | Tearney et al. |
| 6,879,851 | B2 | 4/2005 | McNamara et al. |
| 6,891,984 | B2 | 5/2005 | Petersen et al. |
| 7,208,333 | B2 | 4/2007 | Flanders et al. |
| 7,231,243 | B2 | 6/2007 | Tearney et al. |
| 7,241,286 | B2 | 7/2007 | Atlas |
| 7,397,935 | B2 | 7/2008 | Kimmel et al. |
| 7,414,779 | B2 | 8/2008 | Huber et al. |
| 7,415,049 | B2 | 8/2008 | Flanders et al. |
| 7,593,559 | B2 | 9/2009 | Toth et al. |
| 7,619,646 | B2 | 11/2009 | Freifeld et al. |
| 7,625,366 | B2 | 12/2009 | Atlas |
| 7,729,746 | B2 | 6/2010 | Redel et al. |
| 7,813,609 | B2 | 10/2010 | Petersen et al. |
| 7,848,791 | B2 | 12/2010 | Schmitt et al. |
| 7,916,387 | B2 | 3/2011 | Schmitt et al. |
| 7,935,060 | B2 | 5/2011 | Schmitt et al. |
| 8,116,605 | B2 | 2/2012 | Petersen et al. |
| 8,206,377 | B2 | 6/2012 | Petroff |
| 8,298,147 | B2 | 10/2012 | Huennekens et al. |
| 8,325,419 | B2 | 12/2012 | Schmitt |
| 8,358,461 | B2 | 1/2013 | Huber et al. |
| 8,412,312 | B2 | 4/2013 | Judell et al. |
| 8,449,468 | B2 | 5/2013 | Petersen et al. |
| 8,478,384 | B2 | 7/2013 | Schmitt et al. |
| 8,478,387 | B2 * | 7/2013 | Xu ............... 600/477 |
| 8,503,844 | B2 | 8/2013 | Petersen et al. |
| 8,581,643 | B1 | 11/2013 | Schmitt |
| 8,582,109 | B1 | 11/2013 | Schmitt |
| 8,582,619 | B2 | 11/2013 | Adler |
| 8,582,934 | B2 | 11/2013 | Adler et al. |
| 8,687,201 | B2 | 4/2014 | Adler |
| 8,786,336 | B1 | 7/2014 | Schmitt |
| 8,831,321 | B1 | 9/2014 | Elbasiony |
| 8,948,228 | B2 | 2/2015 | Adler |
| 8,953,911 | B1 | 2/2015 | Xu et al. |
| 2002/0115931 | A1 | 8/2002 | Strauss et al. |
| 2002/0161351 | A1 | 10/2002 | Samson et al. |
| 2005/0201662 | A1 | 9/2005 | Petersen et al. |
| 2005/0238067 | A1 | 10/2005 | Choi |
| 2006/0095065 | A1 | 5/2006 | Tanimura et al. |
| 2006/0165270 | A1 | 7/2006 | Borgert et al. |
| 2006/0203859 | A1 | 9/2006 | Cable et al. |
| 2006/0241465 | A1 | 10/2006 | Huennekens et al. |
| 2006/0244973 | A1 | 11/2006 | Yun et al. |
| 2007/0167710 | A1 | 7/2007 | Unal et al. |
| 2007/0293932 | A1 | 12/2007 | Zilla et al. |
| 2008/0100612 | A1 | 5/2008 | Dastmalchi et al. |
| 2009/0027051 | A1 | 1/2009 | Stuber et al. |
| 2009/0174931 | A1 | 7/2009 | Huber et al. |
| 2009/0204134 | A1 | 8/2009 | Kassab |
| 2009/0306520 | A1 | 12/2009 | Schmitt et al. |
| 2010/0076320 | A1 | 3/2010 | Petersen et al. |
| 2010/0094127 | A1 * | 4/2010 | Xu ............... 600/425 |
| 2011/0071404 | A1 | 3/2011 | Schmitt et al. |
| 2011/0101207 | A1 | 5/2011 | Schmitt |
| 2011/0157686 | A1 | 6/2011 | Huber et al. |
| 2011/0190586 | A1 | 8/2011 | Kemp |
| 2011/0228280 | A1 | 9/2011 | Schmitt et al. |
| 2011/0257545 | A1 | 10/2011 | Suri |
| 2012/0238869 | A1 | 9/2012 | Schmitt et al. |
| 2012/0250028 | A1 | 10/2012 | Schmitt et al. |
| 2012/0310081 | A1 * | 12/2012 | Adler et al. ........ 600/427 |
| 2013/0010303 | A1 | 1/2013 | Petersen et al. |
| 2013/0012811 | A1 | 1/2013 | Schmitt et al. |
| 2013/0023761 | A1 | 1/2013 | Petroff |
| 2013/0051728 | A1 | 2/2013 | Petroff |
| 2013/0072805 | A1 | 3/2013 | Schmitt et al. |
| 2013/0303910 | A1 * | 11/2013 | Hubbard et al. ........ 600/443 |
| 2013/0310698 | A1 | 11/2013 | Judell et al. |
| 2014/0018669 | A1 * | 1/2014 | Xu ............... 600/424 |
| 2014/0024931 | A1 | 1/2014 | Winston et al. |
| 2014/0094697 | A1 | 4/2014 | Petroff et al. |
| 2014/0114182 | A1 | 4/2014 | Petersen et al. |
| 2014/0142427 | A1 | 5/2014 | Petroff |
| 2014/0142432 | A1 | 5/2014 | Hutchins et al. |
| 2014/0142436 | A1 | 5/2014 | Hutchins et al. |
| 2014/0187929 | A1 | 7/2014 | Schmitt et al. |
| 2014/0218742 | A1 | 8/2014 | Adler |
| 2014/0249407 | A1 | 9/2014 | Adler et al. |
| 2014/0268167 | A1 | 9/2014 | Friedman et al. |
| 2014/0276011 | A1 | 9/2014 | Schmitt et al. |
| 2014/0309536 | A1 | 10/2014 | Douk et al. |
| 2014/0379269 | A1 | 12/2014 | Schmitt |

OTHER PUBLICATIONS

Unal et al., "Stent implant follow-up in intravascular optical coherence tomography images", Int J Cardiovasc Imaging, DOI 10.1007/s10554-009-9508-4, published online Sep. 24, 2009 (8 pages).

Xu et al., "Characterization of atherosclerosis plaques by measuring both backscattering and attenuation coefficients in optical coherence tomography", Journal of Biomedical Optics, 13:3, May/Jun. 2008 (8 pages).

Takano et al., "Evaluation by Optical Coherence Tomography of Neointimal Coverage of Sirolimus-Eiutine Stent Three Months After Implantation," American Journal of Cardiology, 99:8, Apr. 14, 2007, pp. 1033-1038.

International Search Report and Written Opinion of the International Searching Authority for International Application No. PCT/US2013/029855 mailed Jun. 17, 2013 (10 pages).

* cited by examiner

STENT VISUALIZATION AND MALAPPOSITION DETECTION SYSTEMS, DEVICES, AND METHODS

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease.

OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be deployed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An underinflated or malapposed stent may fail to restore normal flow. Clearly, after a stent is installed, stent malapposition and under expansion of the stent can result in various problems.

There are other challenges associated with stent placements and related procedures. Visualizing a stent deployment relative to the wall of a blood vessel using an angiography system is challenging to undertake by inspection. Further, reviewing images manually to determine stent position on a per image basis is also prone to error. Given the reflective properties of the metal used in the stents, various imaging artifacts and effects such as blooms or image smearing can result which degrade the images when they occur. These artifacts and effects further compound the difficulty for a user when manually analyzing stents and blood vessel structures.

The present invention addresses these challenges and others.

SUMMARY

In part, the invention relates to computer-based methods, systems and devices for visualizing and measuring stent position relative to a blood vessel wall. In one embodiment, detecting a change in position of a stent such as a malapposition of a stent in a blood vessel is performed using a set of OCT image data. The structural components of the stent are referred to as stent struts in one embodiment. A stent may be visualized and measured using OCT data obtained relative to the stented blood vessel and subsequently displayed as stent struts or portions of a stent as a part of a one or more graphic user interface(s) (GUI). Such an interface can include one or more views of a blood vessel generated using distance measurements obtained using an OCT system.

As part of the process of expanding a stenotic region, a stent is introduced into a lumen of the blood vessel having the stenotic region in a closed or collapsed state. Unfortunately, as part of this process, if the balloon or member is not sufficiently expanded part of the stent may not be properly deployed. Under some circumstances, this can result in the stent not making contact with the wall of the vessel. As a result, the stent can be malapposed with a gap between the outer surface of a stent and the vessel wall. This under expanded stent may require subsequent treatments to correct. A threshold can be set as the basis to perform comparisons of separation distances as determined using the lumen border or contour generated as a stage in an image processing pipeline and a stent strut position that has been evaluated or filtered to reduce the unwanted impact of visual artifacts.

Reference frames and imaging artifacts and effects are evaluated to generate inputs and parameters to select a suitable distance metric in one embodiment. The distance metric is used to obtain measurements between stent struts and a wall of the blood vessel to assess the degree of stent malapposition. The selection of such distance metrics and other considerations relating to stent reflections and probe position in the lumen can be used to reduce or compensate for unwanted imaging artifacts and effects. In turn, these factors and software-based methods that incorporate such features can improve image quality and/or measurement accuracy which results in better patient outcomes.

Further, one embodiment of the invention relates to computer-based methods and graphical user interfaces suitable for displaying data collected with respect to a blood vessel and one or more stents. A data collection probe such as an OCT probe can be used to collect the data used to generate images of the blood vessel and one or more stents.

In one embodiment, the invention relates to a method of detecting stent malapposition in a blood vessel. The method includes storing, in one or more memory devices, a stent malapposition threshold; storing, in one or more memory devices, a plurality of cross-sectional images of the blood vessel; detecting one or more stent struts in the plurality of cross-sectional images using a stent detection image data processing module; detecting a boundary of a lumen of the blood vessel by processing the image data using a lumen detection image data processing module; measuring a stent malapposition distance with respect to one or more stent struts using a stent malapposition detection image data processing module; comparing one or more stent malapposition distance; and displaying one or more indicia corresponding.

In one embodiment, the method further includes executing an image data processing pipeline, using one or more computing devices, using one or more computing devices, the image data processing pipeline comprising the lumen detection image data processing module, the lumen detection image data processing module, and the stent malapposition detection image data processing module. In one embodiment, the method further includes compensating for a sunflower effect or a blooming effect associated with light impinging on a detected stent strut by using a distance metric to measure a malapposition distance extending along a perpendicular to the detected boundary of the lumen to the detected stent strut. In one embodiment, the method further includes the step of receiving the stent malapposition threshold using a graphical user interface.

In one embodiment, the method further includes the step of generating an indicia indicative of the stent malapposition threshold being exceeded for a detected stent strut. In one embodiment, the method further includes the step of generating a first indicia indicative of the stent malapposition threshold being met or being exceeded for a detected stent strut. In one embodiment, the method further includes the step of displaying a cross-sectional view of the blood vessel, the detected stent strut and the first indicia. In one embodiment, the first indicia is a first color and one or more pixels used to display the stent strut are of the first color. In one embodiment, the method further includes the step of generating a second indicia indicative of the stent malapposition threshold being met or not being exceeded for a detected stent strut. In one embodiment, the method further includes the step of displaying a first longitudinal image of the blood vessel oriented in a first direction.

In one embodiment, the method further includes the step of displaying a second longitudinal image of the blood vessel oriented in a second direction. In one embodiment, the method further includes the step of displaying an indicia indicative of a stent malapposition threshold being exceeded on a per detected strut basis. In one embodiment, the method further includes the step of detecting a guidewire and displaying an indicia indicative of the guidewire or a guidewire shadow relative to one or more displayed stent struts. In one embodiment, the method further includes the step of generating a vector having a distance such that the vector is perpendicular to a lumen border, wherein the vector is generated using a measurement of a shadow region for a stent strut.

In one embodiment, the invention relates to an automatic processor-based system for detecting stent malapposition on a per stent strut basis. The system includes one or more memory devices; and a computing device in communication with the memory device, wherein the memory device comprises instructions executable by the computing device to cause the computing device to: process, one or more image detection software modules, a plurality of images obtained from an optical coherence tomography pullback with respect to a blood vessel using a data collection probe such that a lumen border and a plurality of stent struts are detected; store a stent malapposition threshold value in one or more memory devices; generate a plurality of measurements perpendicular to and extending from the lumen border to a detected stent strut; and determine one or more instances of stent strut malapposition by comparing the malapposition threshold value to one or more of the plurality of measurements.

In one embodiment, the computing device includes further instructions to cause the computing device to displaying a first longitudinal image of the blood vessel oriented in a first direction and a second longitudinal image of the blood vessel oriented in a second direction. In one embodiment, the one or more instances of stent strut malapposition are displayed on the first longitudinal image of the blood vessel using one or more indicia. In one embodiment, the one or more instances of stent strut malapposition are displayed on a visual representation of the blood vessel as a panel in a user interface.

In one embodiment, the computing device includes further instructions to compensate for a sunflower imaging artifact using a projection of a stent strut on an ellipse. In one embodiment, the computing device includes further instructions to detect a guidewire and display an indicia indicative of the guidewire or a guidewire shadow relative to one or more displayed stent struts.

In one embodiment, a distance from one or more detected stent struts and a detected luminal boundary is measured along a perpendicular line segment or perpendicular vector having a length extending from the detected luminal boundary to an the detected stent strut. The value of such a distance can be zero or within a set limit or threshold such that no malapposition has occurred or the value can be nonzero and indicate malapposition in one embodiment. This measurement can be performed on a per scan line basis in one embodiment. In one embodiment, the measurement is performed such that the end point associated with a given stent strut is set based on detected stent related values such as stent strut position, a shadow region dimension, a stent strut dimension or other detected stent strut related parameters. A thickness or an angle measurement is an example of such a detected stent related value.

A normalization process can also be used as part of the measurement of the distance between the stent strut and the lumen boundary that includes fitting stent strut position to an ellipse to compensate for the position of the data collection probe in the lumen. Specifically, the normalization process is configured to compensate for the sunflower effect or eccentric catheter position related effects which can lead to imaging artifacts. Each detected stent strut has a dimension such as a shadow thickness or other measurable dimension which can be projected on an ellipse which tracks the stent boundary formed by the stent struts as actually disposed relative to the lumen of the vessel. In one embodiment, each detected stent struts represents a point in a two dimensional space which can be used to model an ellipse that represents a two dimensional cross section of the stent which can be projected on an ellipse which tracks the stent boundary formed by the stent struts as actually disposed relative to the lumen of the vessel.

A detected stent strut dimension can be used to model or projected on to an ellipse to which the stent struts have been fitted to correct for imaging probe position relative to the stent. The project can be performed, in one embodiment, by transforming the detected dimension to a projected dimension on the ellipse. In one embodiment, the detected stent strut dimension is the length of a shadow region between a first stent strut and a second stent strut. This projection can be performed by treating the detected dimension as the hypotenuse of a right triangle. If the angle between the hypotenuse and the projected dimension is S, the projected dimension is product of the cosine of angle S and the hypotenuse.

In one embodiment, a software-based image data processing module is responsive to a malapposition distance threshold. This threshold can be set as an input in response to which a software component in an imaging pipeline automatically detects stent struts and calculates malapposition from a lumen contour. Each stent strut can be coded using an indicia such as a color corresponding to a perpendicular distance from the detected lumen boundary to the detected stent strut.

A user specified distance threshold provides a distance value which indicates that a level of malapposition exists. This distance value can be set such that meeting or exceeding its value corresponds to a malapposition level that necessitates a corrective procedure such as re-stenting, re-inflation, or another procedure. In another embodiment, setting the malapposition threshold indicates a level of malapposition occurring using a visual cue in a graphic user interface. The malapposition threshold can be set on a per user basis. The threshold can be set using a user interface and be updated before, during or after a pullback is complete.

For example, values that range from about 100 microns to about 1000 microns can be specified as such a malapposition distance threshold. In addition, the malapposition distance threshold can be greater than or equal to about 10 microns. In another embodiment, the malapposition distance threshold can be set as an integer multiple of or a fraction of a stent strut thickness. Thus, the threshold can be set as one times, two times, three times or another multiple of a stent strut thickness value. These values are examples and greater or smaller values can be used in some embodiments.

In one embodiment, a sequence of a plurality of image processing software modules including a malapposition detection software module is configured to operate automatically on OCT image data. In one embodiment, the term "automatically" means without human intervention. Notwithstanding the foregoing, the scope of the terms discussed herein is not intended to be limiting, but rather to clarify their usage and incorporate the broadest meaning of the terms as known to those of ordinary skill in the art.

In one embodiment, the malapposition detection software module calculates a plurality of perpendicular line segment measurements and scores them relative to a malapposition threshold. The scores correspond to the level of malapposition which is then mapped or used to alter a display mode for the stent struts to show each struts relative malapposition relative to the vessel wall. These per stent strut malapposition scores can be shown using various indicia or scales such as a color scale or other indicia. In one embodiment, the values or scores are shown by changing the appearance of displayed pixels of the stent struts that appear in a longitudinal viewing mode or a cross-sectional viewing mode of an OCT image.

The software modules and stent malapposition detection and display features described herein can be implemented using a non-transitory computer-readable storage medium. In one embodiment, the non-transitory computer-readable storage medium stores a program that, when executed by a computing device, causes the computing device to perform a method for processing or otherwise operating upon OCT image data. The method can include one or more of the steps outlined herein.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

Figure 1A:
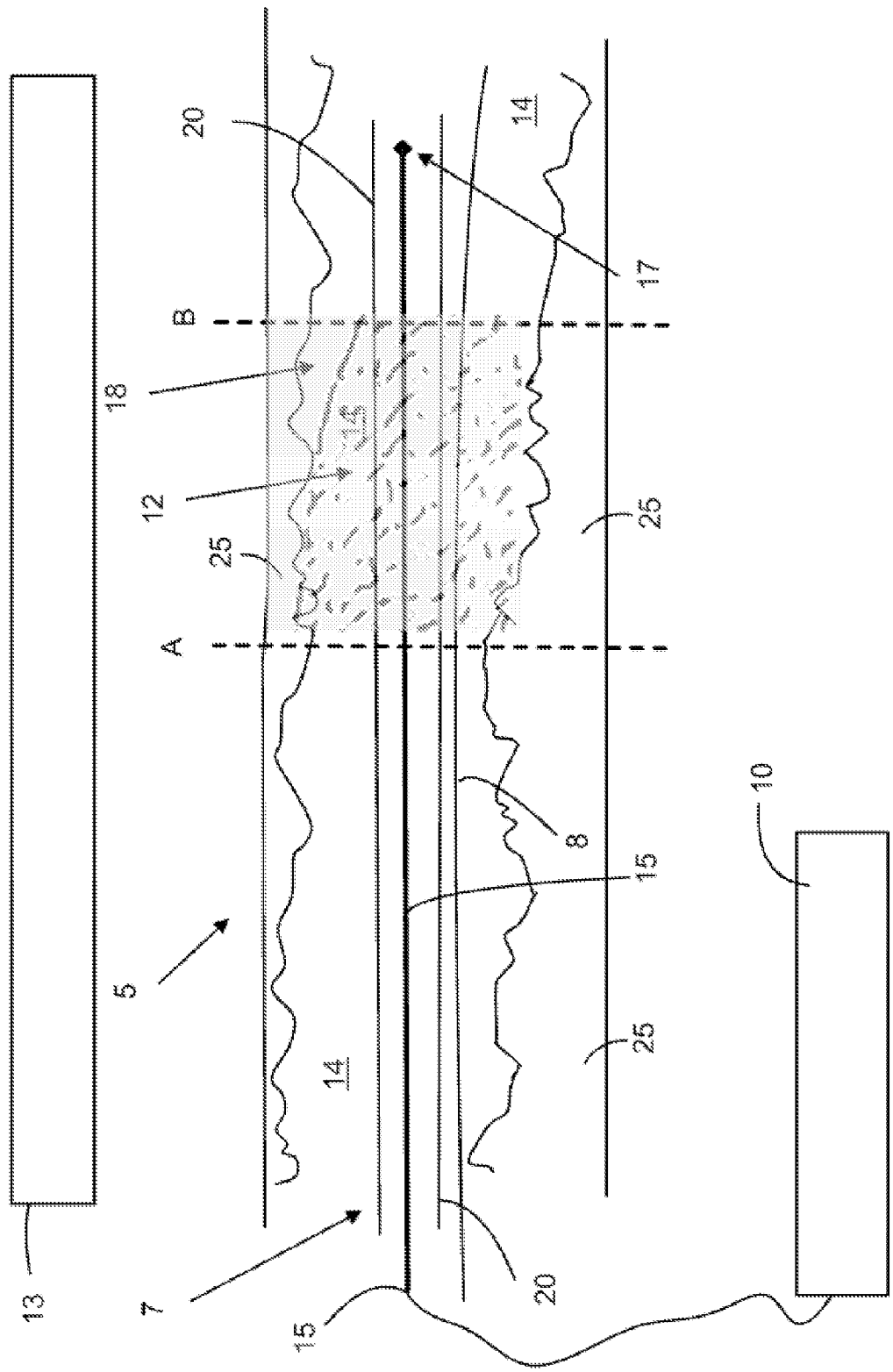
FIG. 1A is a schematic diagram of a data collection system and a data collection probe positioned relative to a stent in a blood vessel in accordance with an illustrative embodiment of the invention.
Figure 1B:
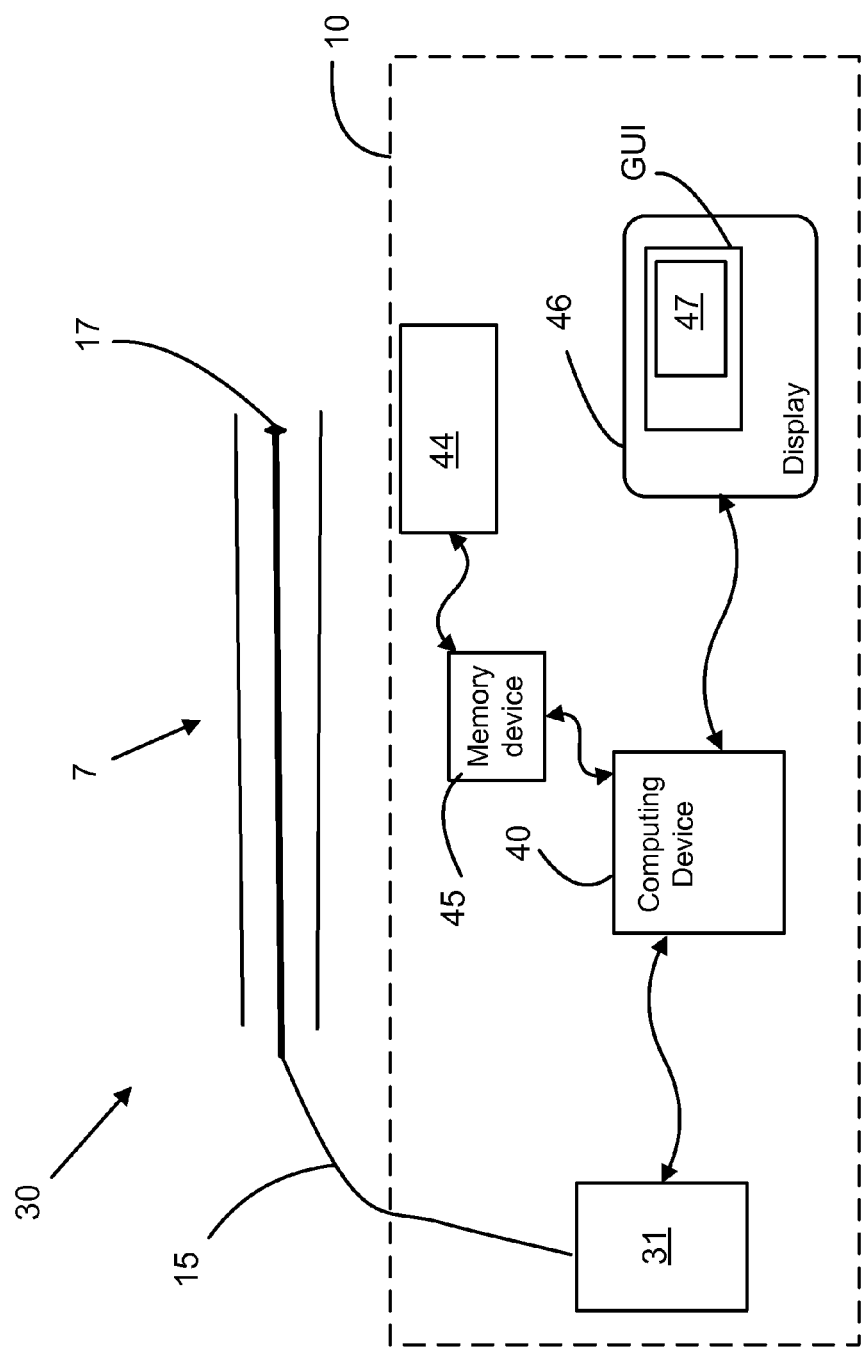
FIG. 1B is a schematic diagram of data collection system and a data collection probe in accordance with an illustrative embodiment of the invention.

Optical coherence tomography (OCT) is an imaging modality that uses an interferometer to obtain distance measurements relative to a sample such as, for example, a blood vessel or objects disposed therein. As shown in FIGS. 1A and 1B, a blood vessel 5 can be imaged using a data collection probe 7. A guidewire 8 can be used to introduce the probe 7 into the blood vessel 5 as shown in FIG. 1A.

The data collection probe 7 can be introduced and pulled back along a length of a blood vessel 5 while collecting data. As the optical fiber is retracted (pulled-back) along the length of the vessel, a plurality of scans or OCT data sets are collected as the probe or a portion thereof rotates. This is referred to as a pullback in one embodiment. These data sets can be used to identify regions of interest such as a stenosis or a deployed stent such as stent 12.

In one embodiment, the data collection probe 7 is an OCT probe configured for use with an OCT system 10 that includes an interferometer and a data processing system. The distance measurements collected using the OCT probe 7 can be processed to generate frames of image data such as cross-sectional views or longitudinal views (L-mode views) of the blood vessel. For clarity, a cross-sectional view can include without limitation a longitudinal view. These images can be processed using one or more image data processing modules or stages such as outlined herein.

For a blood vessel 5 as shown in FIG. 1A, which includes a stent 12 disposed in the lumen 14 of the blood vessel various types of data collection probes and related OCT systems can be used. In one embodiment, the OCT system 10 includes a processor, memory, or other components configured to execute various data processing stages or modules. These stages or modules operate upon and transform image data. These modules or stages can include a stent detection software component and a stent malapposition detection component. A given stent and components thereof can be visualized to include an indicia or measurement of the degree of contact or lack of contact between one or more stent struts, which are components of the stent, and the wall of a blood vessel. One area showing a degree of stent malapposition with respect to stent 12 and wall 26 is shown in region 18. Additional details relating to these features are described herein.

As shown in FIG. 1A, for a given blood vessel, the walls of the vessel define a lumen in which blood flows. X-ray based imaging modalities such as provided by angiography system 13 can be used to image blood vessels and facilitate stent deployment or stent visualization. In addition, as described herein a probe 7 suitable for insertion in a blood vessel 5 can be used to generate images of sections of a given blood vessel. Areas of stenosis or previously deployed stents such as stent 12, which is disposed in lumen 14, can be viewed using various cross-sectional and three-dimensional views of a blood vessel obtained with an OCT system and associated data collection probe.

FIG. 1A is a high level schematic diagram depicting a data collection probe and an OCT system 10 suitable for performing side branch detection, lumen detection, guide wire detection and various other processes. The OCT system 10 can include a suitable light source that satisfies the coherence and bandwidth requirements of the applications and data collection described herein. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 14 such as an arterial lumen. The probe 7 can include a rotating or slidable fiber 15 that directs light forward into the lumen 14 or at a direction perpendicular to the longitudinal axis of the fiber 15. As a result, in the case of light that is directed from the side of the probe as the fiber 15 rotates, OCT data is collected with respect to the walls 25 of the blood vessel 5. The walls of the blood vessel 25 define a lumen boundary. This lumen boundary can be detected using the distance measurements obtained from the optical signals collected at the probe tip 17 using lumen detection software component. The probe 7 can include other imaging modalities in addition to OCT such as ultrasound in one embodiment.

Figure 1C:
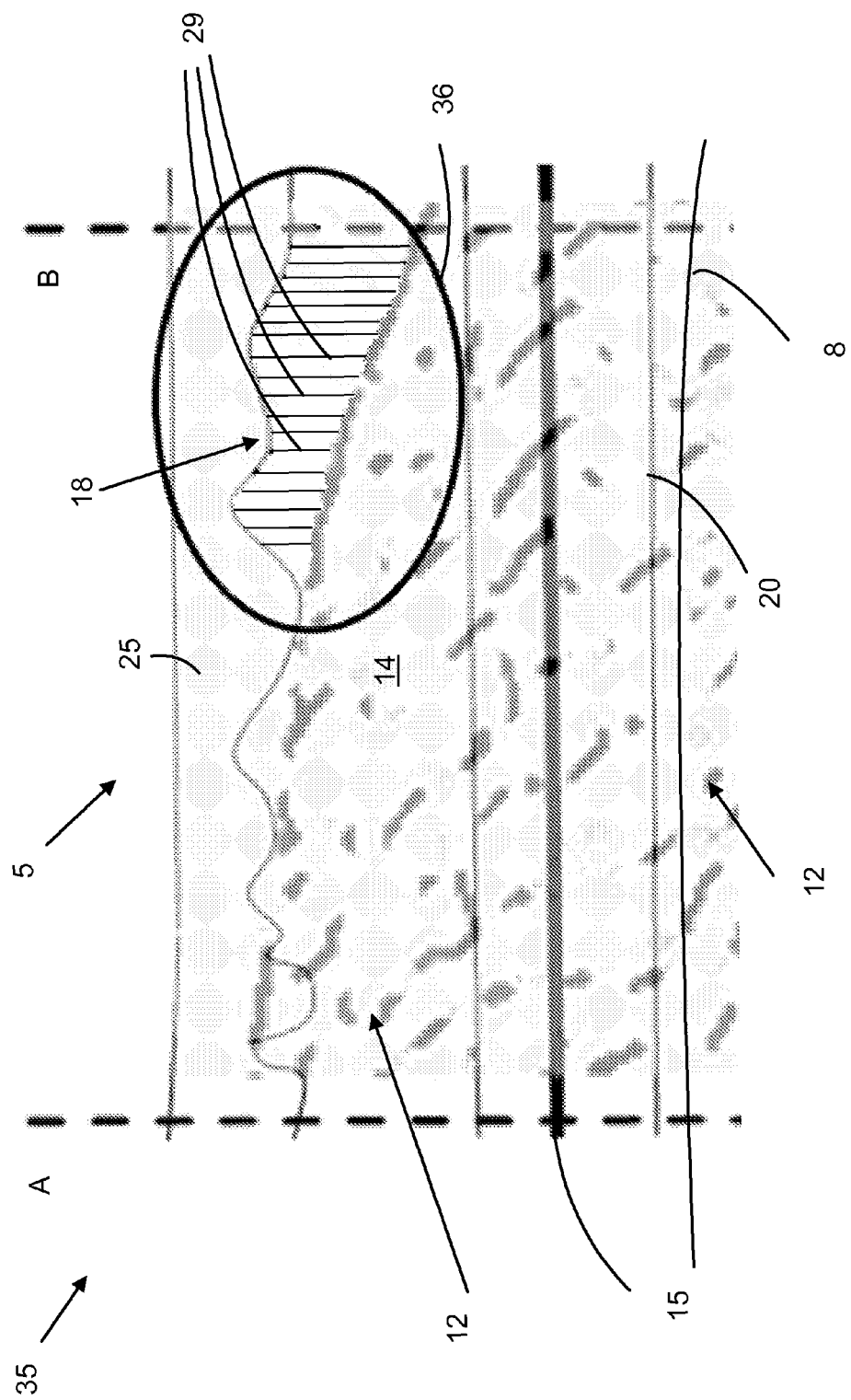
FIG. 1C is a schematic diagram of a portion of a longitudinal view of a deployed stent generated using optical coherence tomography data in accordance with an illustrative embodiment of the invention.

As shown in FIG. 1A, the probe tip 17 is positioned in the lumen 14 such that it is distal to a stented region of the blood vessel 5, which is bounded by dotted lines A, B. Additional details to a similar stent region are also shown in FIG. 1C. The probe tip 17 is configured to transmit light and receive backscattered light from objects, such as for example stent 12, and the wall 25 of the blood vessel 5. The probe tip 17 and the rest of the data collection probe 7 are pulled through the lumen 14 such that the tip passes through the stented region defined by lines A, B. In one embodiment, the probe tip 17 or another portion of the probe 7 can include a pressure sensor such that pressure readings can be obtained at different positions such as distal to line B, between lines A B, proximal to line A, or other positions of interest. Such a pressure transducer can be used to collect pressure data such than an FFR reading can be generated with respect to one or more locations in the vessel 5.

As shown in FIG. 1B, a probe 17 is shown prior to or after insertion in a blood vessel. The probe 7 is in optical communication with an OCT system 10. The OCT system or subsystem 10 that connects to probe 17 via an optical fiber 15 can include a light source such as a laser, an interferometer having a sample arm and a reference arm, various optical paths, a clock generator, photodiodes, and other OCT system components.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for stent visualization, stent malapposition detection, and pullback data collection as discussed below.

Figure 2:
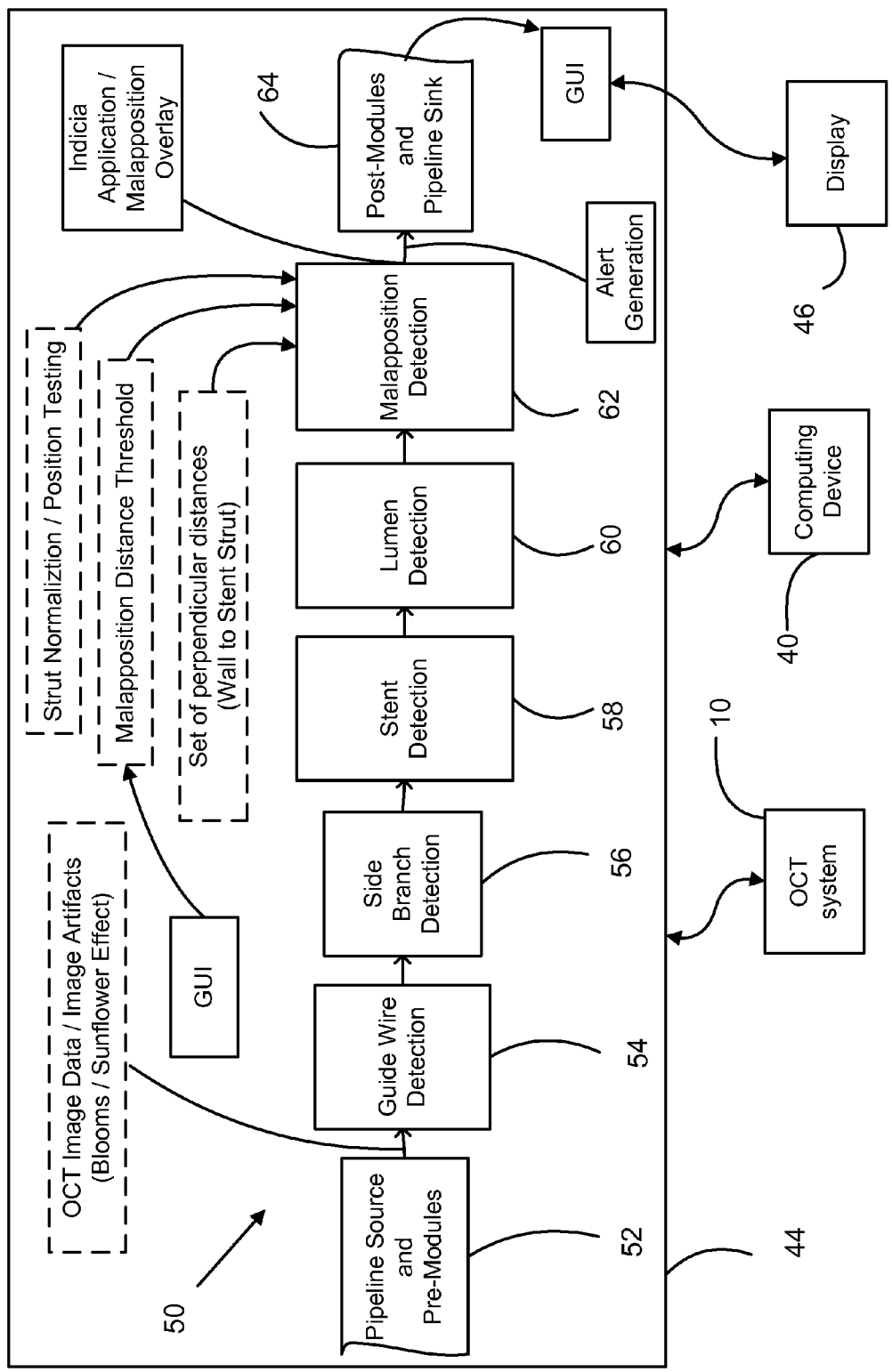
FIG. 2 is a schematic diagram of various software and hardware components including an image data processing pipeline in accordance with an illustrative embodiment of the invention.

In one embodiment, the computing device 40 includes or accesses software modules or programs 44, such as a side branch detection module, a guide wire detection module, a lumen detection module, a stent detection module, a median mask clearing module, an intensity averaging module, a stent malapposition detection module, and other software modules. The software modules or programs 44 can include an image data processing pipeline or component modules thereof and one or more graphical user interfaces (GUI). An exemplary image processing pipeline 50 for transforming collected OCT data into two dimensional and three dimensional views of blood vessels and stents is depicted in FIG. 2. The image data processing pipeline or any of the methods described herein are stored in memory and executed using one or more computing devices such as a processor, device, or other integrated circuit.

As shown, in FIG. 1B, a display 46 can also be part of the system 10 for showing information 47 such as cross-sectional and longitudinal views of a blood vessel generated using collected OCT data. This OCT-based information 47 can be displayed using one or more graphic user interface(s) (GUI). In addition, this information 47 can include, without limitation, cross-sectional scan data, longitudinal scans, diameter graphs, image masks, shadow regions, stents, areas of malapposition, lumen border, perpendicular distances measured relative to a automatically detected lumen border and a perpendicular distance extending from the lumen border to a detected stent strut position, and other images or representations of a blood vessel or the underlying distance measurements obtained using an OCT system and data collection probe. The computing device 40 can also include software or programs 44, which can be stored in one or more memory devices 45, configured to identify stent struts and malapposition levels (such as based on a threshold and measured distance comparison) and other blood vessel features such as with text, arrows, color coding, highlighting, contour lines, or other suitable human or machine readable indicia.

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in FIG. 1C and FIGS. 3A-5. The images of the blood vessel generated using the distances measurements obtained from the OCT system provide information about the blood vessel and objects disposed therein.

Accordingly, in part, the invention relates to software-based methods and related systems and devices suitable for evaluating and depicting information regarding a blood vessel, a stent or other vascular information of interest. The OCT data can be used to generate 2-D views such as cross-sectional and longitudinal views of a blood vessel before or after an initial stent deployment or corrective stent related procedure. The OCT data obtained using a data collection probe and various data processing software modules can be used to identify, characterize, and visualize a stent and/or one or more properties relating to the stent and/or the lumen in which it is disposed.

Stent position and malapposition relative to the wall of the blood vessel can be visualized using a one or more indicia for identifying or distinguishing stent struts. In one embodiment, the step of identifying or distinguishing stent struts is performed by marking points or regions associated with a particular stent strut or group of stent struts on a graphical user interface with a particular pattern such as a color, symbol, or other visible indicia. The points or regions can be displayed as one or more pixels shown in a cross-sectional or three-dimensional view of a blood vessel having a stent deployed therein such as a stent 12.

Further, once such a two-dimensional or a three-dimensional image has been generated or the underling measurements are available in a data store, such as a database or memory device, measurements can be obtained relative to the blood vessel and stent to further enhance diagnosis efforts. For example, measurements relating to a stent such as a degree of stent malapposition can be generated automatically using OCT data without a need for a user to engage in a per strut or per frame calculations. Examples of transforming an image generated using OCT data and further processing such an image using software modules such as stent detection module and a stent malapposition module are shown in FIG. 3A, 3B, 4A, 4B, 6 and others.

In one embodiment, as shown in FIG. 1A, the angiography system 13 can be used to obtain a high level view of the blood vessel of interest. This step can precede or occur simultaneously with the pullback of the rotatable OCT probe. In one embodiment, a fractional flow reserve (FFR) reading can be obtained to see if the blood vessel is requires a stent or if re-stenting or another procedure should occur in light of a level of stent malapposition occurring above a threshold such as a user specified threshold. In one embodiment, a user specified stent malapposition threshold is entered by or selected by a user through a GUI.

As an example of such a procedure, once the software has automatically determined and displayed stent malapposition information to a user, the user may elect to use a balloon in a deflated state. The balloon can be positioned with the aid of the angiography system 13 and used to inflate the balloon to change the stent state and reduce the level of malapposition. Inflating a balloon is not always ideal if there has been stent migration or a significant degree of stent malapposition. Another OCT pullback can be performed to review an installed stent in one embodiment. Stent detection, stent position and lumen detection can be performed using a plurality of software modules arranged in an image data processing pipeline with images or OCT data as the inputs such as, for example, shown in FIG. 2.

Figure 6:
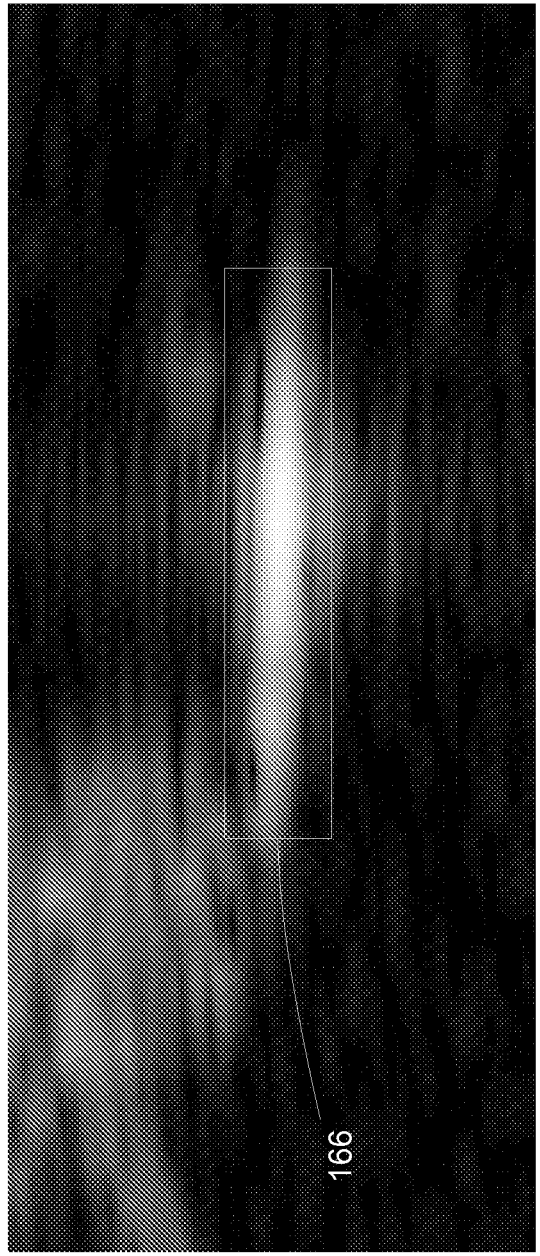
FIG. 6 is a magnified version of a stent strut within a cross-sectional view of an OCT image of a blood vessel obscured by a blooming artifact which can be compensated for in accordance with an illustrative embodiment of the invention.

A three-dimensional image or a two dimensional cross-section of a given blood vessel can be generated using the OCT data collected using a probe 5 and one or more associated OCT subsystems or components. Examples of three-dimensional tomographic images of an artery generated using such a probe are shown in FIGS. 4A and 4B. These images include indicia such as a green (G), yellow (Y), and red (R) color to identify different levels of stent malapposition relative to a specified threshold. FIG. 3B and FIG. 6 shows a two-dimensional cross-section of a vessel having a stent. Each image shown in FIGS. 3A, 4A and 4B has been processed using an image data processing pipeline and a stent detection module or stage as described below.

As shown in FIGS. 1A, 1B and 1C, the probe collects data during a pullback with respect to stenotic regions, blood vessel walls, and stent struts. The optical data enters the probe via a probe tip in one embodiment. The probe tip can include beam directors such as lenses or reflectors or combinations thereof are part of the probe and used to direct the beam on to the vessel wall. The probe tip also receives the scattered light that returns from the vessel wall. The optical information received at the probe tip, which is in optical communication with the sample arm of an interferometer, is subject to various types of noise or other effects. In turn, such noise and effects can lead to imaging artifacts such as blurred or smeared regions when cross-section images of the blood vessel and stent components are generated.

Figure 8:
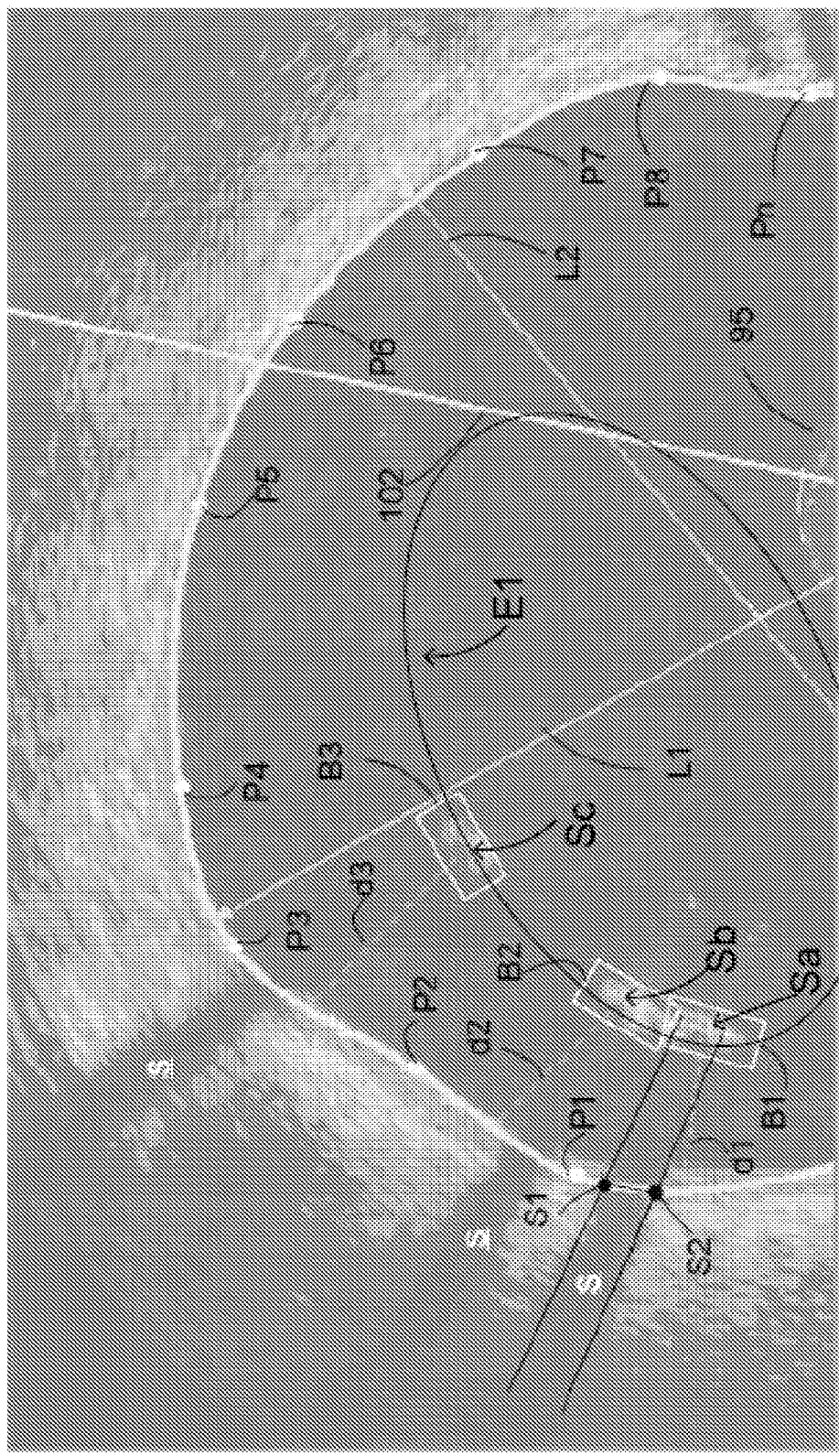
FIG. 8 is a cross-sectional view of a blood vessel shown as part of a graphical user interface in which perpendicular distance measurements between a detected lumen border and a plurality of stent struts are shown in accordance with an illustrative embodiment of the invention.

Given the high reflectivity of various stent materials and other parameters, stents and OCT image data that are correlated with stents can be identified as a cue or other indicia corresponding to a stent. A given stent strut has corners and side surfaces that serve as areas for light from the probe tip to back scatter and cause blooms or light bleeding. These blooms obscure the exact position the stent strut in a given OCT image of the vessel and stent. Exemplary blooms relative to a stent strut is shown in FIGS. 6 and 8.

The blooming visual artifacts associated with stent struts can make it difficult to identify the accurate radial position of the stent and thus can impede manual efforts to review OCT generated images to determine malapposition. From an optical and OCT perspective, a strut is a point that the laser impinged on such that light is scattered back from it with an associated intensity. Due to the intensity saturation caused by the high reflectivity of the metallic stent material, a blooming artifact appears at the position of the stent strut where a single point is expected. In one embodiment, the most intense point of light within the blooming region, is where the inner surface (facing the catheter of the imaging probe) of the strut is located.

Since the OCT data is acquired as a finite number of scan lines, which are distributed in a circular pattern, there are gaps in between the spoke-like arrangement of scan lines. As a result, bilinear interpolation or other types of interpolation are performed between scan lines. The blooming effect is further exaggerated by the interpolation process performed when converting the scan lines to cross-sectional views of a lumen. As a result, blooming artifacts can be more pronounced. Limitations on imaging resolution can also increase the appearance of a blooming artifact. If a stent strut is positioned relative to a gap in between scan lines, this can lead to additional blurring or smearing of the image which is further degraded as a result of the interpolation.

Under some circumstances, as a result of image data being collecting using a rotating probe tip, the alignment of the stent struts can be arranged toward the probe. As a result, the struts can appear to radiate outward from the stent surface. This visual artifact has been analogized to the way sunflowers turn toward the sun. Accordingly, the term sunflower effect can be used to refer to such an alignment related visual artifact. In part, embodiments of the invention reduce the error associated with interpolation related errors, blooming artifacts, and sunflower artifacts.

For those that perform manual calculations using an inner surface or other feature of each bloom to identify a stent strut, the malapposition distances are erroneous because these image features are visual artifacts and can have various geometries which mask the actual stent strut position. Errors in stent strut position further increase errors when performing a stent malapposition distance measurement between such a position and a detected lumen border. Embodiments of the invention reduce such errors and improve the accuracy of malapposition measurements used by clinicians.

An OCT-based imaging system uses light that does not penetrate metal. As a result, a false thickness resulting from the blooming effect can occur on a per stent strut basis. This can result in a stent on two-dimensional cross-sectional images having a thickness instead of being depicted as a point or line. This is shown by the bloom B of FIG. 8. For example, a given blooming can be about 50 microns in thickness. This blooming thickness, which is significant relative to the scale of the malapposition threshold, such as a 400 or 500 micron threshold value, can add significant error to a malapposition distance measurement for a given stent strut. This follows because manual analysis of such struts may use the edge of the bloom to make such a measurement.

In addition to the blooming artifacts, another visual effect which can obscure an image of a stent strut is the sunflower effect. The sunflower effect can occur as a result of the position of the data collection probe in the lumen which changes strut appearance. The data collection probe is off center relative to a central axis of the lumen. As a result, light impinging on a stent from the probe tip may scatter from a stent strut of such an angle other than a right angle.

Identifying the stent position relative to the imaging artifacts which tend to obscure them is challenging. For example, the blooming effect and the sunflower effect can cause stent position to be rendered uncertain as a result of imaging artifacts that are generated in the OCT images prior to such images being input into an image processing pipeline such as the exemplary embodiment of FIG. 2. As a result, configuring the malapposition detection module or another software component used to process OCT image data to use a distance metric that avoids the uncertainty associated with blooming thickness or the sunflower effect is beneficial. Additional details relating to such a distance metric and obtaining perpendicular measurements relative to the vessel wall to mitigate such unwanted optical effects are described herein.

As shown in FIG. 1C, the area of the vessel 5 of FIG. 1A in which a stent 12 is disposed, between lines A and B, in the lumen 14 is magnified. This magnification can be performed using a zoom or magnification software module. As shown, by the plurality of measurable line segments 29 there is a region of separation 18 from the wall of the vessel 5 showing the degree to which the stent 12 has pulled away or is otherwise malapposed.

This localized pulling away can occur over time or can be an indication of an underinflated stent during the initial stent deployment. In one embodiment, about 500 microns is set as a threshold or limit such that a distance measured with respect to a line segment 29 extending from and perpendicular to the lumen border to a detected stent strut that equal or exceed about 500 microns trigger an alert or other indication on a graphic user interface or other communication indicative of malapposition. Such an alert or communication can be used to prompt further analysis or a procedure such as removing the stent or re-stenting.

An OCT image, such as the cross-sectional images of FIGS. 3A, 3B, 3C, 5 and 6 are typically acquired one scan line at a time. A sequence of samples along a ray originating at the catheter center to the maximum imaging depth is referred to as a scan line. Thus, a given scan line can correspond to a one-dimensional cue or indicia of a stent strut or stent portion. A cross-sectional image is formed by a collection of scan lines as the probe rotates.

In one embodiment, for non-overlapping stents, a stent strut is one point in the collection of points for a given scan line. A cross-sectional image can be formed from a set of scan lines collected as the probe rotates. Further, to image a segment of an artery or other vessel, the catheter is moved longitudinally while rotating. In this way, the probe acquires a set of cross-sectional images in a spiral pattern.

The resultant two and three dimensional images originate from the various scan lines associated with a slice of the vessel or artery of interest. The image can be displayed as cross-sections, such as in FIG. 3A-3C. The combination of cross-sectional images allow a tomographic image such as the three-dimensional perspective views of a vessel in FIGS. 4A and 4B to be automatically generated using software that operates on or otherwise transforms the OCT data acquired during a pullback.

Figure 3A:
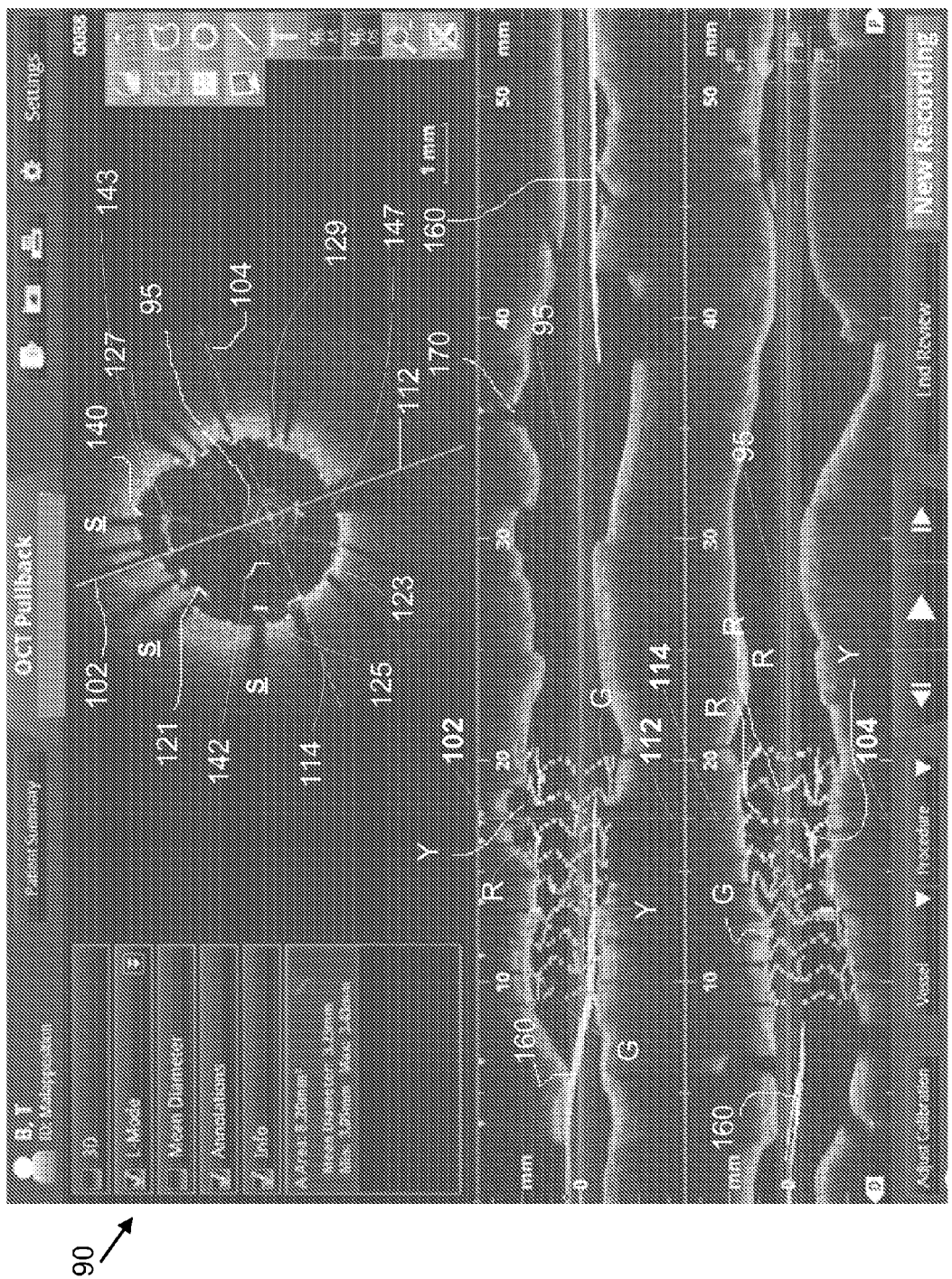
FIG. 3A is a graphical user interface that includes three panels showing cross-sectional views of a blood vessel with malapposition regions identified with indicia in accordance with an illustrative embodiment of the invention.
Figure 3B:
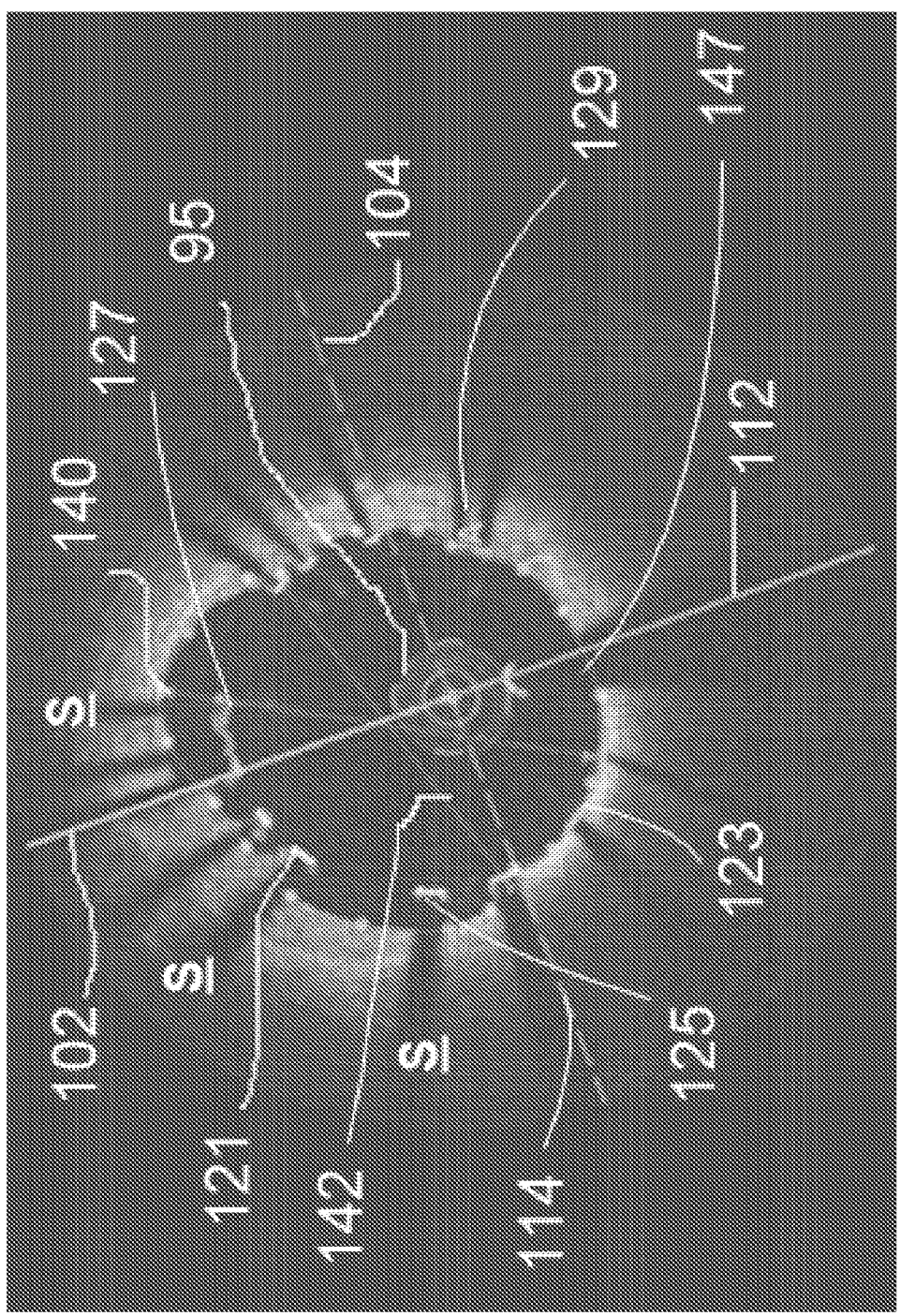
FIG. 3B is magnified view of a cross-sectional OCT image view of the graphical user interface of FIG. 3A in accordance with an illustrative embodiment of the invention.
Figure 4A:
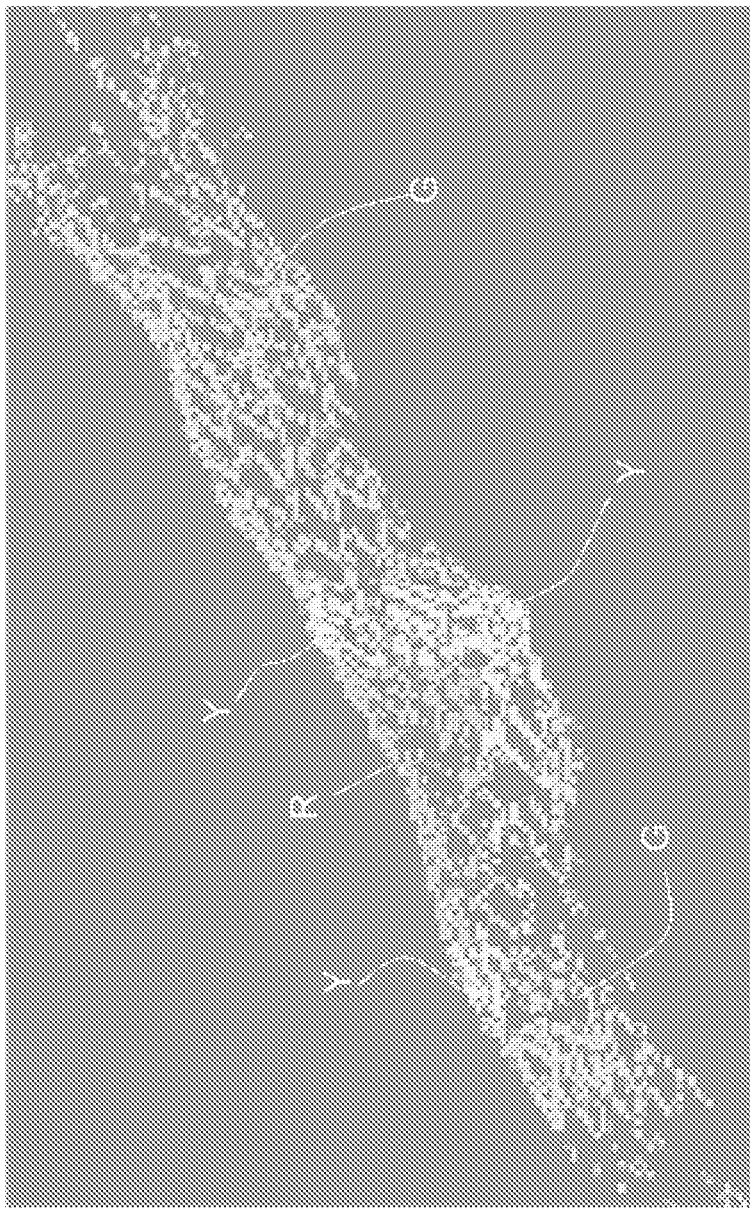
FIGS. 4A and 4B are three-dimensional views of a blood vessel with malapposition regions coded with different indicia in accordance with an illustrative embodiment of the invention.
Figure 4B:
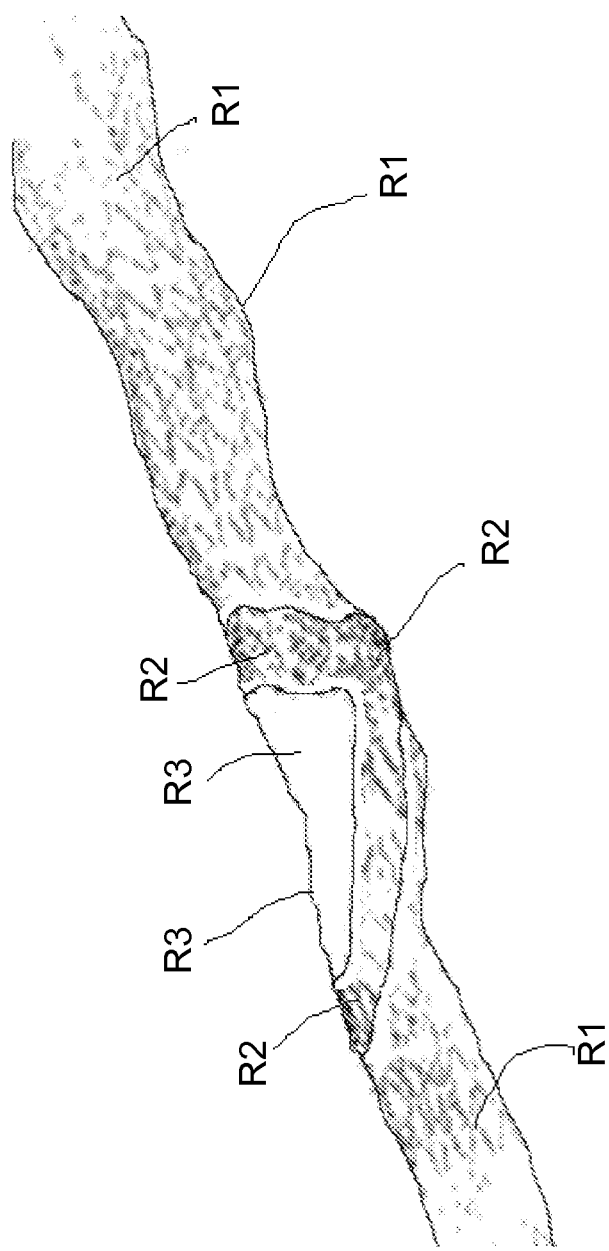

FIG. 3A shows a graphic user interface 90 configured to review images that have been generated based upon the interferometrically obtained distance measurements and subsequently analyzed and processed by one or more software components. For example, such software components can include one or more of the image data processing modules of FIG. 2. The interface 90 can include one or more panels configured to display a view of the vessel such as cross-sectional view shown in the middle top panel and the two longitudinal views shown in the bottom two horizontal panels.

The cross-sectional view of the blood vessel includes various lines or axes 102, 112, 104, 114 which serve to provide a reference frame such that the first and second longitudinal views below can be reconciled relative to a cross-sectional view. In addition, as another landmark a component of the data collection probe 95 is also shown in the lumen of the blood vessel. The guidewire 160 along which the probe is advanced into a lumen is shown in one embodiment as projection in a longitudinal image of the vessel.

Figure 7A:
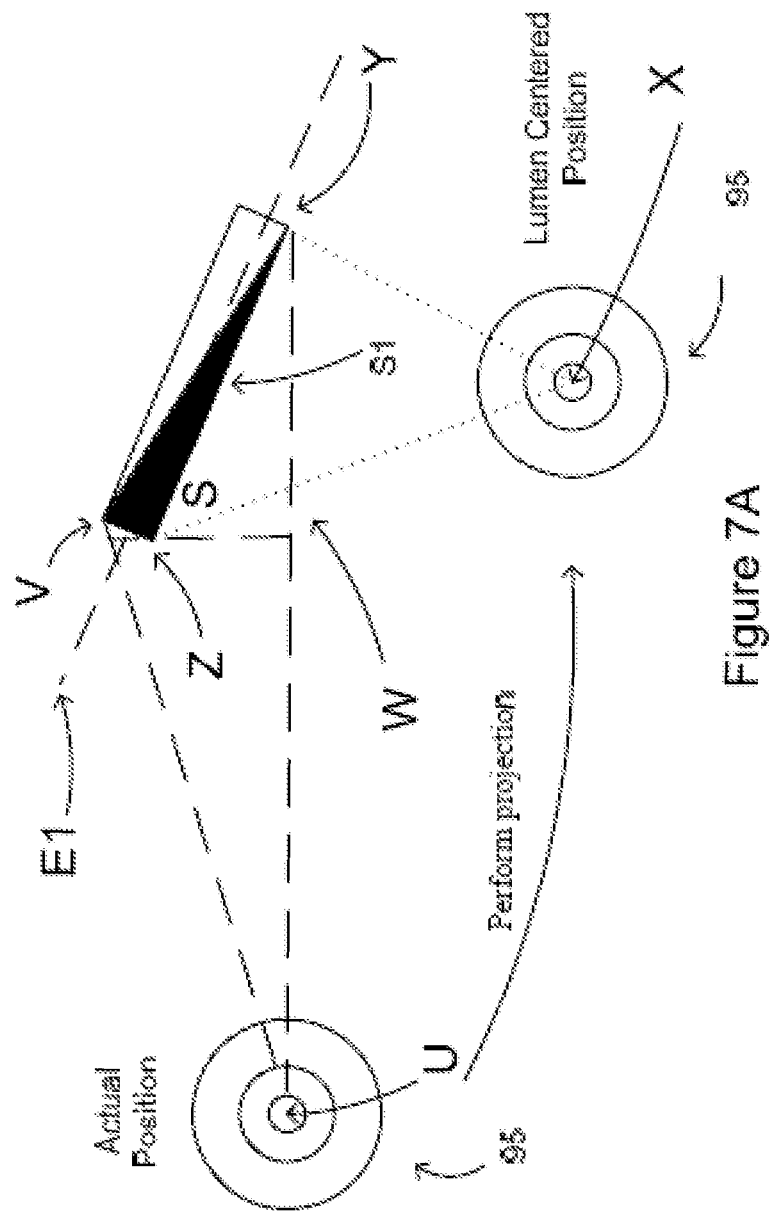
FIG. 7A is a schematic diagram of data collection probes in two orientations, one actual and one exemplary, relative to a stent strut to illustrate how the sunflower effect can be compensated for in accordance with an illustrative embodiment of the invention.

A cross-section of a data collection probe 95 having one or more sheaths such as the sheath of a catheter is shown disposed within a blood vessel and a stent. The probe serves as a reference point in the figure. The probe 95 includes the rotatable optical fiber which collects the data used to generate scan lines and the cross-sectional image shown. As discussed in more detail herein, the position of the probe 95 can be off center relative to the center of the blood vessel. An example of this is shown in FIG. 7A in which an actual position of the probe is displayed relative to an ideal lumen centered position. This off center positioning can result in the sunflower effect relating to stent strut imaging as described herein. As shown, in FIG. 3A, the user interface 90 includes various cut planes, cut plane angles and other measurements as shown by the line segments displayed in the top, middle, and bottom panels.

For example, the line segment formed by segment 102 and segment 112 corresponds to a cut plane of the blood vessel being displayed at a first cut plane angle. The slice of the blood vessel shown at the cut plane angle in the first panel corresponds to the slice of the blood vessel shown in the middle panel with the same two line segments 102 and 112. The cut plane angle used in the middle panel determines which portion of the vessel cross-section is viewable to the user. In one embodiment, the cut plane angle and/or the cut plane are selected to show a relative extrema or an overall maximum amount of stent malapposition for the stent containing frames of image data.

In one embodiment the first segment 102 is color-coded with a first color such as yellow and the second segment 112 is color-coded with a second color such as blue. A second line segment, which intersects, the first segment is shown as a dotted line in FIG. 3A. This second axis includes a first segment 104 and a second segment 114 which can also be color-coded or otherwise modified by suitable indicium. In addition, as shown in FIGS. 3A and 3B, line segment 142 corresponds to the minimum lumen diameter in the cross-section shown while line segment 143 corresponds to maximum lumen diameter shown.

Line segments 102, 112, 104, 114 denote the angled cut planes that divide the blood vessel along as shown by the two longitudinal views of the middle panel and the bottom panel. In this way, the one cross-sectional area in the upper panel of FIG. 3A, which is also shown in FIG. 3B, corresponds to the first longitudinal view of FIG. 3C in which 102 is in the top half and 112 is in the bottom half of the associated longitudinal view of the blood vessel. In the second longitudinal view of FIG. 3C the other half of the vessel is shown. These different views as well as the three-dimensional views in FIGS. 4A and 4B can be used to show stent struts coded with an indicia corresponding to a degree of malapposition.

In one embodiment, the indicia used are G, Y, and R which can be symbols or the colors green, yellow, and red, respectively, or other identifiers. The pixels of the displayed stent struts can be colored based on these indicia in one embodiment. In one embodiment, the G indicium corresponds to an amount of malapposition less than a malapposition threshold. In one embodiment, the R indicium corresponds to an amount of malapposition greater than a malapposition threshold. In one embodiment, the Y indicium corresponds to an amount of malapposition in between the amounts associated with the G and R indicia. In one embodiment, the Y indicium corresponds to a projection of one or more shadows generated by the guidewire 160. In one embodiment, G can be used to indicate that there is no malapposition based upon the specified threshold.

As shown in FIG. 4B, other indicia can be used to identify regions of the stent associated with different levels of malapposition such as shown by indicia R1, R2, and R3. Stent struts can be displayed using suitable indicia such as a color code or symbolic or texture code applied to a region of pixels associated with one or more stent struts. Stent struts reflect light but do not transmitted into the vessel wall which results in the formation of shadows S which extend behind a given stent strut into the vessel wall. For example, as shown in FIG. 3B, stent strut 121 generates shadow S as shown. Similarly, stent strut 125 generates shadow S as shown. Stent strut 127 generates shadow S as shown. Each of these three stent struts 121, 125, and 127 are shown disposed within the lumen in contrast with other stent struts shown as closer to or substantially in contact with the vessel wall such as stent struts 123, 129, and 140.

The interface 90 can also include various indicia or other features that can be superimposed upon cross-sectional and longitudinal views. These views can be toggled on and off using various menus or selectable controls such as clickable or checkable boxes. For example, the panel to the left of the cross-sectional view of the blood vessel includes various selectable features as follows 3-D, L mode, mean diameter, annotations, and information. In one embodiment, selecting 3-D, results in a perspective view of the vessel such as shown in FIG. 4A or 4B being generated. In one embodiment, the OCT image data is processed using the image data modules or stages of FIG. 2 such that a three-dimensional profile of an imaged blood vessel and a stent relative to a lumen boundary can be detected and displayed.

In one embodiment, the software includes an initial display software routine with preset image selection filters or conditions that specify which images of a blood vessel are shown to a user. In one embodiment, when pullback data is loaded following collecting from a data collection probe certain features are selected to display to a user as part of the user interface. For example, in one embodiment, in the event there is a stent in the blood vessel or in the event there is a malapposed stent, one or more of the vessel cross-sectional views are displayed to the user such that a cut plane angle is set to automatically provide a cross-sectional view of the stent having the largest amount of malapposition. In this way, the software presents a user with a view that helps them assess a region of interest in the vessel without having to perform a frame by frame analysis to reach frames containing a stent malapposition. In one embodiment, the cutplane that divides the blood vessel and establishes the view by which a user can review two L-mode views is automatically set to present a view of detected stent struts showing the largest amounts of malapposition relative to the vessel wall.

In one embodiment, the software searches for frames of image data that satisfy certain filters or conditions. These filters or conditions can include, without limitation, a frame or set of frames of image data having a stent, a frame or set of frames of image data showing a relative extrema of malapposition, a frame or set of frames of image data showing a maximum degree of malapposition, a frame or set of frames of image data showing a minimum degree of malapposition, a first longitudinal view showing a first region of stent malapposition from a first view or first viewing angle, or a second longitudinal view showing the first region of stent malapposition or a second region of stent malapposition from a second view or second viewing angle. In one embodiment, the software is configured to display two halves of a stent using two longitudinal views as an initial view presented to a user. Thus, a distal view looking down a half or another fraction of a vessel can be shown relative to, such as above or below or adjacent to, a proximal view looking down another half or fraction of the vessel at an angle showing stent malapposition.

The system and software-based method described herein can process frames of optical coherence tomography data obtained with respect to a blood vessel such that a stent disposed in the blood vessel can be evaluated or otherwise characterized. In one embodiment, each cross-sectional image can constitute a frame of OCT image data. For example, in one embodiment such a stent is identified on a graphic user interface showing a three-dimensional or two-dimensional image of the blood vessel generated using collected OCT data.

For example, in FIGS. 4A and 4B different regions of the stent shown in these figures are malapposed relative to the vessel wall to varying degrees as indicated by the indicia shown. A separation distance or detachment measurement between a stent strut and a section of the vessel wall can be measured using the OCT image data and compared to a malapposition threshold. This distance measurement can be used to represent a stent malapposition or another stent state such as under inflation or tissue overgrowth.

A region of the image corresponding to no malapposition of the stent can be coded using colors or other indicia as described herein. In one embodiment, green (G) is used to indicate no malapposition or a small amount of malapposition below a certain threshold. In one embodiment, red is used to indicate malapposition or an amount of malapposition above a certain threshold.

Figure 3C:
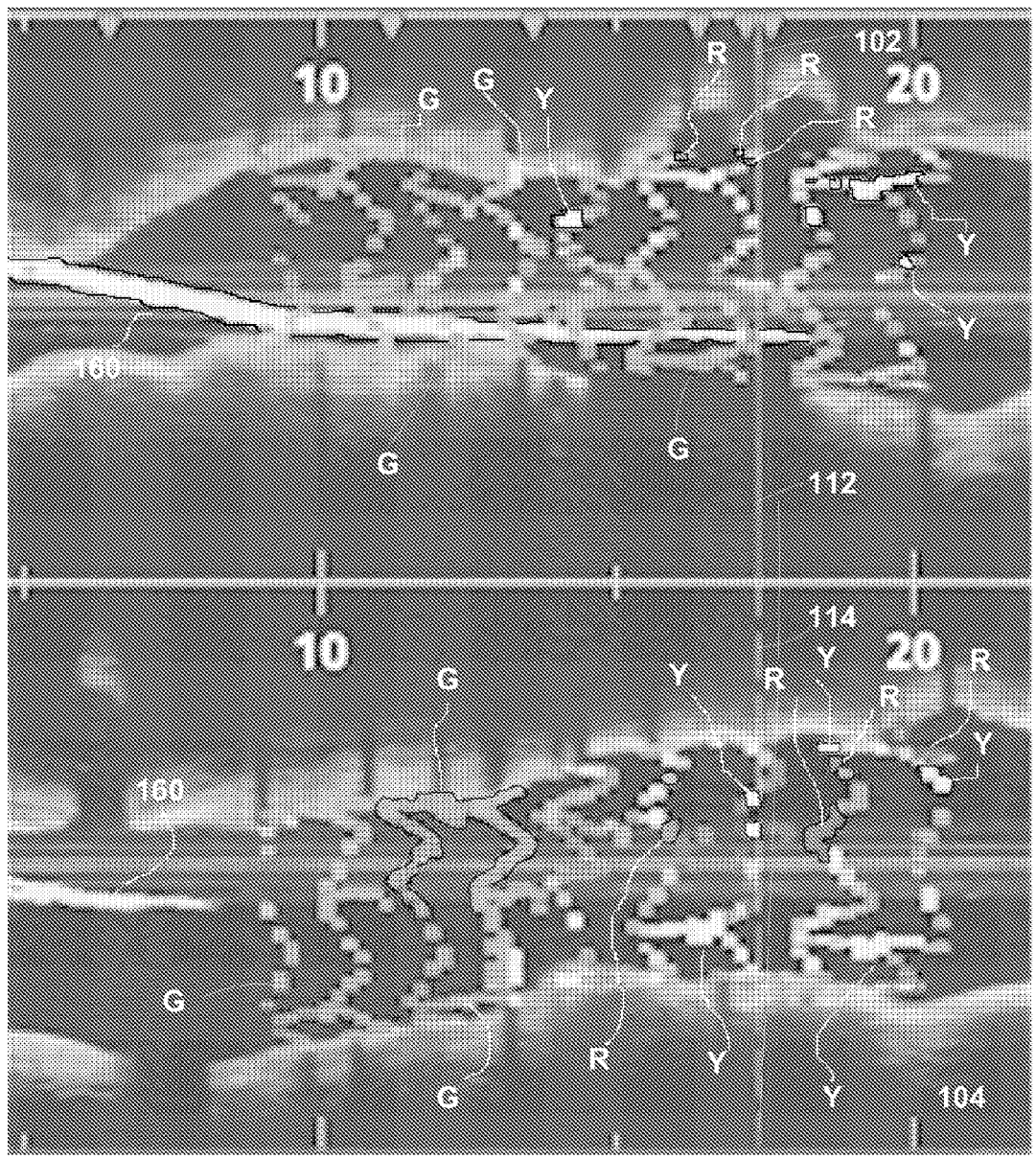
FIG. 3C is magnified view of the two longitudinal cross-sectional OCT image views of the graphical user interface of FIG. 3A in accordance with an illustrative embodiment of the invention.

In one embodiment, as shown in FIGS. 3A and 3C, two L modes or longitudinal views are displayed to show either side of the stent and the associated malapposition that is localized to one section of the stent. The pixels associated with a given stent strut can be coded using a color map. The relatively smaller number of areas having an indicia corresponding to a specified threshold not being met is evidenced by a larger amount of the G indicia, such green colored pixels, in the stent strut image and a smaller number of the R red indicia such as red colored pixels. By displaying the two longitudinal modes of the blood vessel with the indicia and the guide wire 160, an operator is able to look down either side of the blood vessel and interpret the malapposition of the stent struts.

In FIG. 2, a high level of overview of an image data processing pipeline and other inputs, outputs, and system components are shown. In one embodiment, raw image data is generated from the data collected from an interferometer in optical communication with an OCT probe. The data can be collected using a detector such as a photoreceiver. The image data processing pipeline 50 includes various processing stages or modules that operate on the image data to accomplish a particular objective. In one embodiment, stent malapposition detection is implemented as such a stage or module 62 in the image data processing pipeline 50.

A malapposition software module 62 can be configured to calculate regions of significant malapposition with respect to a stent and the vessel wall. The malapposition module is configured to compare a distance threshold, such as one or more thresholds described herein, or another user specified threshold with a distance measured from the vessel wall to a stent strut. The relative comparison between the threshold and the measured distance can be used to apply an indicia to the stent strut based on the threshold being met or exceeded. The indicia are indicative of the level of malapposition relative to that stent strut and the vessel wall or a detected lumen border.

As shown in the exemplary image data processing pipeline 50 of FIG. 2, the pipeline 50 includes a pipeline source and pre-modules. The pipeline source receives data from an OCT system that includes distance information relative to a sample of interest such as depth measurements along the wall of an artery. The pipeline can also include various pre-processing modules such as formatting or noise correcting modules or other filters. The pipeline source and the pre-processing modules 52 are placed ahead of other modules or stages shown in one embodiment. The data in the pipeline can include OCT image data such as a plurality of cross-sectional views generated using OCT distance measurements that include blooms and other imaging artifacts.

The modules or stages shown include guide wire detection 54, side branch detection 56, stent detection 58, and lumen detection 60, and malapposition detection. Since the guidewire is a continuous feature running through the pullback frames which causes shadows and other visual effects, it is detected first in one embodiment. Side branches appear as dark or shadow regions in an OCT image. Therefore, in one embodiment, side branch detection 56 is performed using a side branch detection module 56 to identify the side branches because stent struts may be obscured by the shadow region associated with the side branch. This follows because the shadow of a stent strut is used for stent detection in one embodiment. If the shadows of a stent strut and a side branch overlap or otherwise blend together one large combined shadow region can result. By performing side branch detection first, the image processing pipeline can then be configured to detect one more stent struts within a region and know whether or not the region at issue includes a side branch shadow. Additional detection steps and filters can be used with the knowledge that a stent strut may be positioned in a side branch area or be obscured by a side branch shadow.

Although this order is preferred in one embodiment, other orders are possible, and the modules and stages can be combined or divided into different software-based modules, stages or applications. A pipeline sink and the post-processing modules 64 are arranged after the modules or stages shown. A pipeline sink 64 can include an output module configured to display images on a display or other device such as the views shown as part of the graphical user interfaces described herein.

In one embodiment, the sequence of software modules shown in FIG. 2 are configured to operate automatically on the image data generated using the OCT scan lines obtained during the pullback. A cross-sectional image is created for each complete turn of the probe. In one embodiment, the data associated with a given frame of OCT data is processed sequentially by the data processing modules in order from left to right as shown in FIG. 2. In other embodiments, the data can be processed in other batches, data sets, or in the aggregate. Given that each cross-sectional image of the blood vessel contains geometric relationships between the walls of a vessel, detected stent struts, detected side branches, detected lumen border, and detected stent malapposition can be generated using the pipeline 50 on a per cross-section basis.

Figure 5:
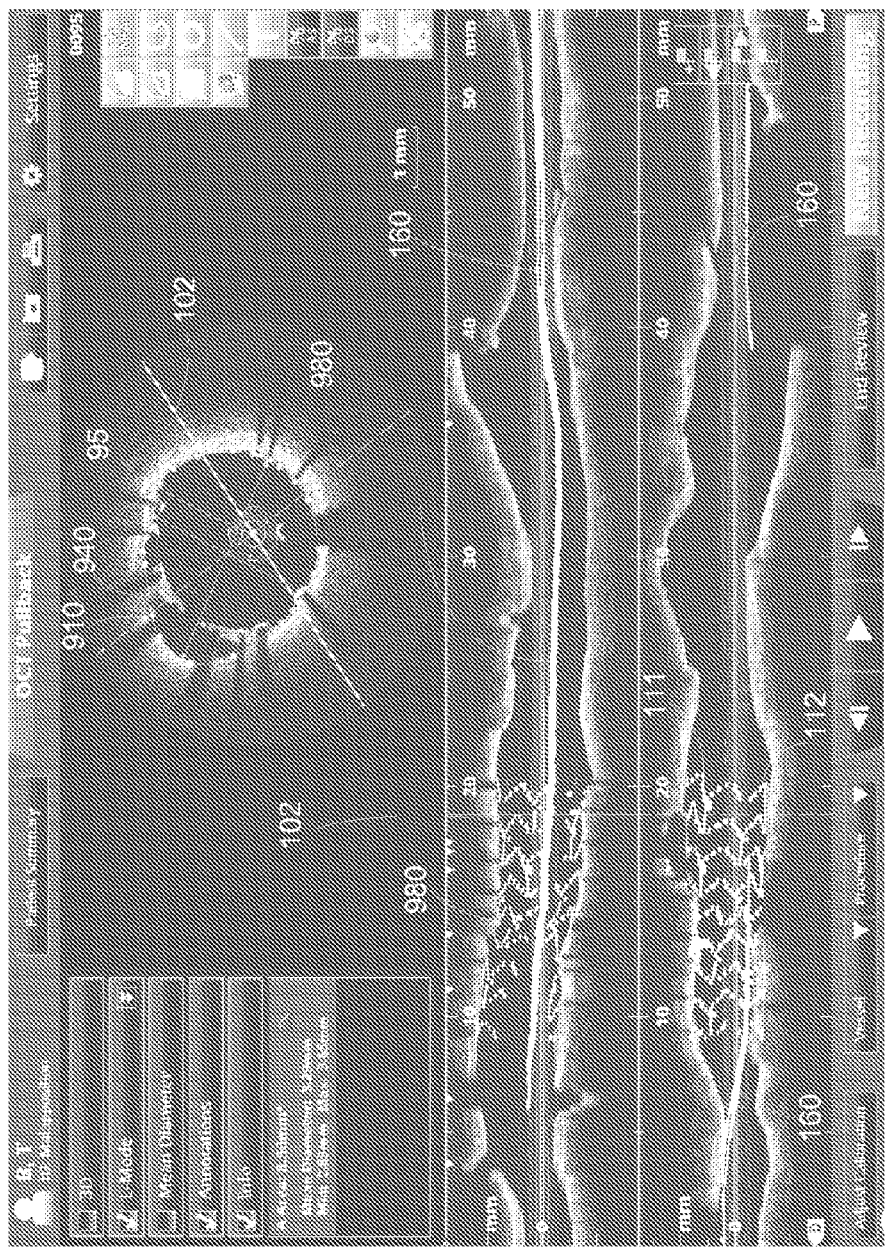
FIG. 5 is a graphical user interface that includes three panels showing cross-sectional views of a blood vessel with malapposition regions identified with indicia and a projection of a guidewire in accordance with an illustrative embodiment of the invention.

As discussed herein, detecting and visualizing the guidewire is desirable because it allows the guidewire 160 to be projected in an OCT image, such as in FIG. 5, to provide context for blind spots and other effects that occur due to shadows from the guidewire. The guidewire detection module 54 operates on OCT image data and detects the guidewire in the relevant images. In one embodiment, the side branch detection module or stage 56 is next used on the image data as discussed above prior to stent detection module 58 being run. In one embodiment, lumen detection is performed using a lumen detection module 60 after stent detection in order that stents struts can be excluded as candidate points for the lumen boundary. Thus, the software module for lumen detection can be configured to exclude stent struts, once detected, for improved lumen detection.

Stent detection can also be performed relative to the OCT image data using stent detection module 58. As part of the image data processing pipeline, in one embodiment the lumen of the blood vessel is found. Various techniques can be used to detect the lumen such as those disclosed in Methods for Stent Strut detection and Related Measurement and Display Using OCT U.S. Pat. Pub. No. 20100094127, the entire contents of which are incorporated herein by this reference. In addition, in one embodiment, following lumen detection stent strut malapposition is then detected using malapposition detection module 62.

The malapposition detection module 62 calculates malapposition from the automatically detected lumen contour and stent struts. A GUI can be configured such that the user of the system inputs a malapposition threshold for use as basis for comparison when assessing malapposition on a per stent strut basis. In one embodiment, the cut plane angle corresponding to a maximum amount of or relative extrema amount of malapposition is also calculated and presented to the user. In one embodiment, the cut plane refers to the angle at which the initial display is presented to the user. In one embodiment, the module 62 uses a plurality of perpendicular distances relative to the vessel wall and each detected strut to determine incidents of malapposition. In addition, a stent normalization or position testing process can also be implemented to establish correct stent positions for performing a distance measurement. A projection of a detected stent dimension on an ellipse fitted to other detected stents can be used as one step of such an embodiment. This projection and ellipse fitting improves the accuracy of stent strut position which in turn improves malapposition distance calculations performed using stent strut position or orientation. One or more modules in pipeline 50 or other software can also be used to overlay or project indicia onto the cross-sectional images and generate alerts relating to the incidents of stent malapposition.

FIG. 5 shows a cross-sectional image of a blood vessel with a guidewire 160 disposed in the lumen and adjacent the probe. The guidewire casts a shadow that can obscure portions of a stent. Parts of the stent struts, which are obscured by the guidewire shadow, can be accounted for by projecting a guidewire in the image using color or other indicia. In this way, including the guidewire in the image provides context of its position in the vessel. In turn, such a visual representation of the guidewire can help prevent an operator of the system from misinterpreting regions of missing stent data or other image data.

In addition to projecting the detected stent on the L-Mode, projecting a detected guide wire 160 can facilitate detecting blind spots on the projected stent image in places where the guide wire shadow blocks parts of the stent as shown in FIGS. 3A and 3C. These blinds spots are worth identifying because malapposition information relative to such spots is less accurate. In addition, blooming artifacts as shown in the images of FIG. 5 and FIG. 8 also obscure a stent strut and preclude a manual frame by frame measurement approach as a result of all of the errors that accumulate from estimating and a lack of certainty as to where to measure from the stent strut to the vessel wall to obtain a malapposition distance (to the extent malapposition exists).

A stent is effectively a wire mesh tube, which is squeezed when deployed. As a result, a deployed stent has an elliptical cross-section which can include a circular cross-section as a special case of an ellipse. As a result, the detected stent struts should lie on an approximately ellipsoidal shape when displayed in an image. This geometric constraint can be used to perform stent normalization or position testing process in which stent positions are validated by fitting them to an ellipse which tracks the geometry of the overall stent diameter in the applicable cross-sectional image. In one embodiment, candidate stent struts are detected using the relevant software module. Next, an ellipse is fitted to the detected stent struts.

To account for the sunflower effect, a measured stent strut dimension, such as the shadow region measured by an OCT probe, is projected on the fitted ellipse for each stent strut or pair of stent struts. Next, malapposition measurements are calculated using stent strut positions following any correction that occurs from the step of projecting a measured stent strut dimension on the fitted ellipse. For those regions in which the orientation of the stent strut equals that of the fitted ellipse the cosine of the projection angle will be 1 (or approximately or about 1) since the projection angle will be zero (or approximately or about zero). Thus, when the stent strut is already disposed on the fitted ellipse, S is zero (or approximately or about zero).

Figure 7B:
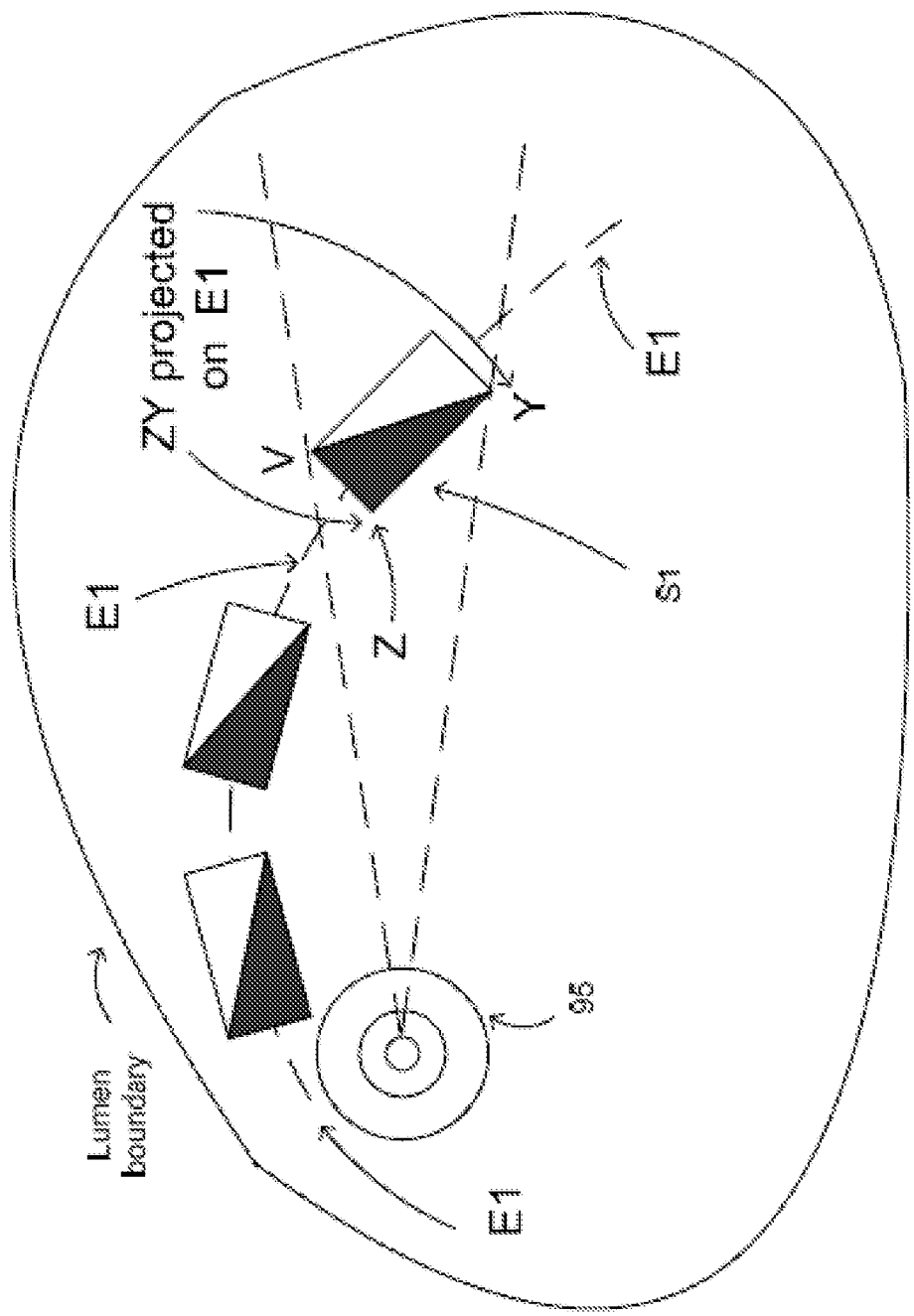
FIG. 7B is a schematic diagram of one data collection probe orientation of FIG. 7A relative to a fitted ellipse upon which a measured dimension of a stent strut has been projected upon in accordance with an illustrative embodiment of the invention.

The sunflower effect can affect the calculated malapposition value. The extent to which it affects the malapposition value can be accounted for using a projection step. Specifically, the software is configured to project a detected strut dimension on an ellipse fitted to the detected stent struts to compensate for position effects of the probe such as the sunflower effect. An exemplary ellipse E1 is shown in FIG. 7B.

FIG. 7A shows an exemplary occurrence of the sunflower effect. In addition, a software implementable feature to compensate for it using a projecting step is also shown. Specifically, a blood vessel is shown having a stent strut S1 in a cross-sectional view. As discussed above, the actual position of a catheter based image data collection probe 95 such as an OCT probe is disposed in the lumen in an off center orientation. This off center orientation is the actual orientation used to collect image data. As a result, from the vantage point shown, the probe 95 rotates and images the stent strut S1 along the scan lines between lines segments UV and UW. As a result, the measured thickness of the associated shadow region that is measured in the image is the distance VW. In addition, looking outward from the probe center point U, the stent strut S1 appears to be almost perpendicular, yet slightly tilted relative, to the probe. The actual border of the stent can be approximated by fitting a curve to the other detected stent struts to generated fitted ellipse E1.

Alternatively, if the probe 95 where in a more centered position as is illustrated by the lumen centered position having center point X, the probe 95 rotates and receives information relating to the stent strut S1 through the scan lines disposed between the line segments ZX and YX. As a result, the actual thickness of the stent strut S1 is the distance ZY. From center point X, the stent strut is oriented as it is positioned in the lumen. The two different sectors of scan lines that are traced as a result of the two illustrated probe positions, centered ay U and X, respectively, result in different thickness measurements and stent strut orientations.

A projection step can be performed using the stent malapposition software module or other software by which the stent strut length corresponding to ZY is projected. As shown, VWY is a right triangle with W being position of the 90 degree angle. The projection angle S corresponding to angle WZY shows a tilt relative to segment ZW. In order to correct for the variations in stent strut measurements that result from the sunflower effect shown in FIG. 7A, the angle S can be used to generate a projection of a corrected stent strut measurement. The product of the (Cosine of S) and distance ZY projects the distance VY along ZW. Other angles and vector projection methods such as dot products and other forms can be used. Conceptually, this is similar to sliding position U to position X with respect to the imaging probes. In this way, the alignment artifacts resulting from imaging from position U twists the stent strut dimension ZY such that it more closely matches the scenario if the imaging were performed from position X. This corrected measurement can then in turn be projected on fitted ellipse E1 which tracks the stent struts detected. Additional details relating to such a projection are shown in FIG. 7B. These software features can be implemented in the stent malapposition detection algorithm of the imaging pipeline shown in FIG. 7B or otherwise as part of the processing of the data collected via the probe.

In FIG. 7B, the stent strut S1 of FIG. 7A is shown in relation to the other detected stent struts which constitute the stent when viewed in cross-section. All of the stent struts shown in FIG. 7B are fitted to ellipse E1. The fitted ellipse E1 allows for the stents strut's orientation to be corrected for prior to performing malapposition distance measurements. Initially, a line can be fit to two stent struts based on the width of the shadow region. This line can be generated as part of fitted ellipse E1. A projection angle can be measured relative to the line between the two stent struts corresponding to the distance and alignment of the stent strut from the imaging position U of the probe. By taking the cosine of the projection angle and multiplying it by the thickness of the stent strut, the stent strut thickness is projected along the fitted ellipse with a corrected orientation.

FIG. 8 shows a cross-sectional OCT image of a blood vessel such as an artery. The border of the lumen of the artery has been identified using image data analysis and the applicable modules. In one embodiment, this image analysis and processing is performed by a lumen detection module in an image data processing pipeline such as pipeline 50.

Several points are disposed along the lumen border P1-Pn are generated by the lumen detection software module. These detected points P1-Pn are outputs from the lumen detection module. These points are connected by curve which is superimposed over the cross-sectional image obtained from the OCT data collection probe. Various shadows from stent struts S are also shown in the cross-sectional blood vessel OCT image. Three stent struts are shown on the left side of the figure.

Boxes identifying the blooms B1, B2, and B3 occurring in the vicinity of each strut Sa, Sb, Sc are also shown. The struts which correspond to part of the stent give rise to the three shadow regions S extending from the curve representing the border of the lumen. Since each strut should be viewable as a point, it is clear that the blooming artifacts add error to the stent strut position. The brightest point within the blooming area on individual scan lines (impossible to assess with the human eye) is automatically identified as the position of the strut.

With respect to each of the three stent struts Sa, Sb, Sc three distance measurements d1, d2, d3 are generated using the stent malapposition detection module. These distance measurements are shown as dotted line segments extending from a stent strut on the ellipse E1 to the curve representing the luminal border. In one embodiment, stent struts Sa, Sb, Sc have been positioned relative to the ellipse E1 using a projection step to compensate for the sunflower effect as described herein. A portion of the sheath 95 of the data collection probe used to generate the cross-sectional image shown in FIG. 6 appears in the bottom of the figure.

Each of the stent struts Sa, Sb, Sc is partially obscured by an imaging artifact. Specifically, the imaging artifacts at issue correspond to blooms B1, B2, B3 and/or the sunflower effect related artifacts. As discussed above herein, the blooming artifacts or blooms result in part from light striking the stent strut and being backscattered to the probe 95 at an angle other than the angle of incidence. This results in a smearing or blurring around stent strut. When operators are performing manual calculations to determine the degree of stent malapposition such blurring or smearing of the image in the vicinity of the bloom reduces the likelihood that the correct measurement point for the stent strut is selected when calculating a malapposition distance relative to the wall lumen. Each shadow region S associated with a stent strut can be measured using points of intersection with the shadow region and the detected boundary such as points S2 and S1 shown in FIG. 8.

As shown in FIG. 8, from the position of luminal border relative to ellipse E1 and the stent struts disposed in the lumen of the vessel it is clear there is a substantial degree of stent malapposition. The stent malapposition detection module of the image data processing pipeline is configured to use a distance metric that mitigates the erroneous position selection and subsequent distance measurement errors that can result from blooming. The blooming artifacts of FIG. 8 create a locus around each stent strut in which the shadow region thickness has an error as well as an error in the point of location of each affected stent strut.

In part, one embodiment of the software is configured to avoid using certain boundary data such as the inner surface of a stent strut bloom as the location of the strut to minimize observer variations. The inner surface of the bloom on the screen can be a visual artifact created by limited resolution as well as bilinear interpolation. Therefore, relying on the inner surface of a bloom is not desirable when measuring stent malapposition. Using such a surface provides another source of inconsistency between a stent malapposition software module and a clinician performing a manual analysis. The use of the methods described herein allows for automatic stent malapposition determination and visualization.

Other methods can include determining chords from a centroid of the lumen. Unfortunately, such chords are only perpendicular to the overall circular shape of the lumen and are not perpendicular to the local variations of the luminal shape. Thus, using such chords to measure malapposition is globally correct but locally inaccurate. As a result, in one embodiment, when calculating the malapposition, the malapposition detection module calculates a local perpendicular distance relative to the vessel wall. These perpendicular distances are shown in FIG. 1C, lines 29, and in FIG. 8, lines d1, d2, and d3. For a given stent strut, such a calculated perpendicular distance is used to determine the amount of malapposition relative to a user specified malapposition distance threshold.

When calculating the distance from the vessel wall for each of the distances 29 shown in 1C generally and the specific distances d1, d2, and d3 shown in FIG. 8, the minimum distance can be determined using various principles as outlined herein. It is useful to specify a function, $f(x)$, that represents the lumen contour curve or border in the xy-coordinate system. In turn, the location of the detected strut is given by the point $(a, b)$. Since any point on the lumen curve would be presented as $(x, f(x))$, the distance D from detected strut position to a point on the curve can be calculated as:

$$D = \sqrt{(x-a)^2 + (f(x)-b)^2} \quad (1)$$

To find the minimum distance, the derivative of D is set to zero $$D' = \frac{2(x-a) + 2(f(x)-b)f'(x)}{\sqrt{(x-a)^2 + (f(x)-b)^2}} = 0 \quad (2)$$

Only the numerator can be zero or $$(x-a) + (f(x)-b)f'(x) = 0 \quad (3)$$

This can be rearranged to, $$f(x) = -\frac{1}{f'(x)}(x-a) + b \quad (4)$$

Where the derivative $f'(x)$ is the slope m of the lumen contour calculated from:

$$f'(x) = \lim_{\Delta x \to 0} \frac{f(x + \Delta x) - f(x)}{\Delta x} = m \quad (5)$$

For the discrete case, $\Delta x$ is chosen to be reasonably locally small value to represent the slope of the curve in the neighborhood of the strut. A reasonable small value is the width of the shadow region. The distance of the shadow region S can be measured as the distance between the two points S1 and S2 (such as shown in FIG. 8) on the luminal border corresponding to the beginning and end of the shadow region. As shown in FIG. 7A, the orientation of a stent strut as viewed by a probe 95 will result in changes to shadow region associated with stent strut. Since this distance S can vary based on the sunflower effect, the techniques described herein relating to ellipse fitting and projection of stent strut dimensions on such an ellipse compensates for positional errors associate with the effect when measuring stent malapposition distances. Thus, in one embodiment, the slope m of the lumen contour is determined using two points on the lumen contour intersecting the shadow edges.

Equation (4) is the equation of the straight line from the strut location to the lumen contour and it satisfies the condition of a perpendicular distance when the slope of the straight line is −1/m where m is the slope of the lumen border or contour.

The strut location, the point (a, b), satisfies equation (4). In addition, the software component handling stent malapposition detection is configured to solve for the other end of the line $f(x)$ that intersects with the perpendicular line representing the contour slope. Since this point satisfies the straight line representing the contour slope, the following relationship holds true:

$$f'(x)(x - x_1) + y_1 = -\frac{1}{f'(x)}(x - a) + b \qquad (6)$$

Where $(x_1, y_1)$ is one of the two points used to calculate the slope. Solving for x then using the slope equation to find y, the point (x, y) on the lumen contour is determined subject to the constraint that such a point provides the minimum distance to the strut location for the calculated local contour slope.

A user can specify a threshold malapposition distance. For example, a user can input a distance value that a given user considers representative of a significant malapposition. The software automatically detects stent struts and calculates malapposition from the lumen border which was automatically detected using a lumen detection module as shown in FIG. 2. The cut plane angle corresponding to the maximum amount of malapposition will be automatically selected and presented to the user as the initial cut plane angle.

In one embodiment, the detected stent is projected on the L-Mode and the calculated malapposition values are presented to the user using a suitable representation. For example, malapposition as a continuous color scale from a given color at zero or less to a different contrasting color at threshold or more on the 2D image as well as the L-Mode projection and the 3D image.

In the description, the invention is discussed in the context of optical coherence tomography; however, these embodiments are not intended to be limiting and those skilled in the art will appreciate that the invention can also be used for other imaging and diagnostic modalities or optical systems in general.

Non-Limiting Software Features and Embodiments for Implementing OCT Methods and Systems The following description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic device, network PCs, minicomputers, mainframe computers, and the like. The invention can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, a algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "detecting" or "measuring" or "calculating" or "comparing" "generating" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present invention, in some embodiments, also relates to apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

Embodiments of the invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, detecting lumen borders, detecting stent struts, comparing measured perpendicular distances relative to set thresholds, and otherwise performing image comparison, signal processing, artifact removal, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, guide wire locations, shadow region locations, side branch locations, side branch diameters, intensity profiles, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

What is claimed is:

1. A method of detecting stent malapposition in a blood vessel comprising:

storing, in one or more memory devices, a stent malapposition threshold;

storing, in one or more memory devices, a plurality of cross-sectional images of the blood vessel;

detecting one or more stent struts in the plurality of cross-sectional images using a stent detection image data processing module;

detecting a boundary of a lumen of the blood vessel by processing the image data using a lumen detection image data processing module;

measuring a stent malapposition distance with respect to one or more stent struts using a stent malapposition detection image data processing module;

comparing one or more stent malapposition distance;

compensating for a sunflower effect or a blooming effect associated with light impinging on a detected stent strut by using a distance metric to measure a malapposition distance extending along a perpendicular to the detected boundary of the lumen to the detected stent strut; and displaying one or more indicia corresponding to a stent malapposition.

2. The method of claim 1 further comprising executing an image data processing pipeline, using one or more computing devices, using one or more computing devices, the image data processing pipeline comprising the lumen detection image data processing module, the lumen detection image data processing module, and the stent malapposition detection image data processing module.

3. The method of claim 1 further comprising the step of receiving the stent malapposition threshold using a graphical user interface.

4. The method of claim 1 further comprising the step of generating an indicia indicative of the stent malapposition threshold being exceeded for a detected stent strut.

5. The method of claim 1 further comprising the step of generating a first indicia indicative of the stent malapposition threshold being met or being exceeded for a detected stent strut.

6. The method of claim 5 further comprising the step of displaying a cross-sectional view of the blood vessel, the detected stent strut and the first indicia.

7. The method of claim 6 wherein the first indicia is a first color and one or more pixels used to display the stent strut are of the first color.

8. The method of claim 6 further comprising the step of generating a second indicia indicative of the stent malapposition threshold being met or not being exceeded for a detected stent strut.

9. The method of claim 1 further comprising the step of displaying a first longitudinal image of the blood vessel oriented in a first direction.

10. The method of claim 9 further comprising the step of displaying a second longitudinal image of the blood vessel oriented in a second direction.

11. The method of claim 10 further comprising the step of displaying an indicia indicative of a stent malapposition threshold being exceeded on a per detected strut basis.

12. The method of claim 10 further comprising the step of detecting a guidewire and displaying an indicia indicative of the guidewire or a guidewire shadow relative to one or more displayed stent struts.

13. The method of claim 1 further comprising the step of generating a vector having a distance such that the vector is perpendicular to a lumen border, wherein the vector is generated using a measurement of a shadow region for a stent strut.

14. An automatic processor-based system for detecting stent malapposition on a per stent strut basis, the system comprising:

one or more memory devices; and a computing device in communication with the memory device, wherein the memory device comprises instructions executable by the computing device to cause the computing device to:

process, one or more image detection software modules, a plurality of images obtained from an optical coherence tomography pullback with respect to a blood vessel using a data collection probe such that a lumen border and a plurality of stent struts are detected;

store a stent malapposition threshold value in one or more memory devices;

generate a plurality of measurements perpendicular to and extending from the lumen border to a detected stent strut;

compensate for a sunflower effect or a blooming effect associated with light impinging on a detected stent strut by using a distance metric to measure a malapposition distance extending along a perpendicular to the detected boundary of the lumen to the detected stent strut; and determine one or more instances of stent strut malapposition by comparing the malapposition threshold value to one or more of the plurality of measurements.

15. The system of claim 14 wherein the computing device comprises further instructions to cause the computing device to displaying a first longitudinal image of the blood vessel oriented in a first direction and a second longitudinal image of the blood vessel oriented in a second direction.

16. The system of claim 15 wherein the one or more instances of stent strut malapposition are displayed on the first longitudinal image of the blood vessel using one or more indicia.

17. The system of claim 14 wherein the one or more instances of stent strut malapposition are displayed on a visual representation of the blood vessel as a panel in a user interface.

18. The system of claim 14 wherein the computing device comprises further instructions to compensate for a sunflower imaging artifact using a projection of a stent strut on an ellipse.

19. The system of claim 14 wherein the computing device comprises further instructions to detect a guidewire and display an indicia indicative of the guidewire or a guidewire shadow relative to one or more displayed stent struts.

* * * * *